US012802807B2

(12) United States Patent
Bhimavarapu et al.

(10) Patent No.: US 12,802,807 B2
(45) Date of Patent: Nov. 17, 2026

(54) SYSTEMS AND METHODS FOR PROVIDING HEALTH INFORMATION

(71) Applicant: Stryker Corporation, Portage, MI (US)

(72) Inventors: Krishna Sandeep Bhimavarapu, Kalamazoo, MI (US); William Dwight Childs, Plainwell, MI (US); Christopher Ryan Sweeney, Portage, MI (US); Annie Désaulniers, Bothell, WA (US)

(73) Assignee: Stryker Corporation, Portage, MI (US)

( * ) Notice: Subject to any disclaimer, the term of this patent is extended or adjusted under 35 U.S.C. 154(b) by 0 days.

(21) Appl. No.: 19/261,447

(22) Filed: Jul. 7, 2025

(65) Prior Publication Data

US 2025/0336509 A1 Oct. 30, 2025

Related U.S. Application Data

(63) Continuation of application No. 17/064,864, filed on Oct. 7, 2020, now abandoned, which is a continuation of application No. 15/295,722, filed on Oct. 17, 2016, now abandoned.

(60) Provisional application No. 62/242,735, filed on Oct. 16, 2015.

(51) Int. Cl.

| | |
|---|---|
| ***G16H 40/40*** | (2018.01) |
| ***G16H 10/60*** | (2018.01) |
| ***G16H 40/20*** | (2018.01) |
| ***G16H 50/30*** | (2018.01) |

(52) U.S. Cl.

CPC ............ *G16H 40/40* (2018.01); *G16H 10/60* (2018.01); *G16H 40/20* (2018.01); *G16H 50/30* (2018.01)

(58) Field of Classification Search

None

See application file for complete search history.

(56) References Cited

U.S. PATENT DOCUMENTS

| | | | | |
|---|---|---|---|---|
| 9,582,838 | B1 * | 2/2017 | Henderson ............. | G16H 40/63 |
| 2004/0128163 | A1 * | 7/2004 | Goodman ............. | G06Q 10/10<br>705/2 |
| 2012/0089419 | A1 * | 4/2012 | Huster .................. | A61G 7/018<br>705/3 |

(Continued)

*Primary Examiner* — Karen A Hranek

(74) *Attorney, Agent, or Firm* — Gardner, Linn, Burkhart & Ondersma LLP

(57) ABSTRACT

A system for providing healthcare information regarding a patient's hospital visit includes a health information application that operates on a plurality of electronic devices. The application displays first data regarding the patient's visit; processes information indicating a current location of the mobile electronic device; and displays second data regarding the patient's visit that is delayed until the mobile electronic device crosses a boundary of a geo-fenced area. The electronic device may also communicate with a bed server at the healthcare facility and authorize the bed server to automatically send a notification message to a second mobile electronic device associated with the patient's friend or family member based on the patient's sleep status and/or movement into or out of bed. The application may also gather and process data useful to healthcare administrators, such as HCAHPS survey scores, status data for medical devices, equipment servicing information, and other information.

20 Claims, 32 Drawing Sheets

(56) References Cited

U.S. PATENT DOCUMENTS

| | | | | |
|---|---|---|---|---|
| 2012/0116803 | A1* | 5/2012 | Reid | G16H 40/20 705/2 |
| 2014/0009271 | A1* | 1/2014 | Collins, Jr. | G07C 3/00 340/286.07 |
| 2014/0259414 | A1* | 9/2014 | Hayes | A61B 5/7275 600/595 |
| 2014/0324451 | A1* | 10/2014 | Pesot | A61B 5/7475 705/2 |
| 2014/0343968 | A1* | 11/2014 | Wilson | G16H 10/60 705/3 |
| 2015/0170494 | A1* | 6/2015 | Hsu | A61B 5/1117 340/539.17 |
| 2015/0302539 | A1* | 10/2015 | Mazar | G08B 21/02 705/3 |
| 2016/0259906 | A1* | 9/2016 | Iucha | A61G 7/00 |
| 2017/0011178 | A1* | 1/2017 | Hendrickson | G16H 40/20 |

* cited by examiner

106b

| Title | Category | Users | Replies | Views | Activity |
|---|---|---|---|---|---|
| How do you know if it's primary cardiac arrest | | 266 | 1000 | 330 | 3h |
| Is this the same as a heart attack? | General | 3 | 12 | 183 | 3h |
| Should I stop compressions if the victim gasps? | | 4 | 0 | 255 | 4h |
| Can you damage someone's heart if you perform CPR while it is beating? | CPR | 3 | 0 | 8 | 7h |
| Why don't you check for a pulse? | Pulse | 6 | 7 | 285 | 8h |
| Don't you need to check the airway first? | | 266 | 1000 | 330 | 3h |
| Do I have to remove a persons clothes to do Chest-Compression-Only CPR or only when using an AED? | General | 3 | 12 | 183 | 3h |
| What if the person has an ICD or a pacemaker? | ICD | 4 | 0 | 255 | 4h |
| How does the victim get oxygen with Chest-Compression-Only CPR? | CPR | 3 | 0 | 8 | 7h |
| What if the person recently underwent open heart surgery, couldn't this crack the chest bone? | | 6 | 7 | 285 | 8h |
| Can I be held liable for performing Chest-Compression-Only CPR? | CPR | 266 | 1000 | 330 | 3h |
| Will chest compressions alone bring the person back or restart the heart? | General | 3 | 12 | 183 | 3h |
| Can this method be used in all arrests? | | 4 | 0 | 255 | 4h |
| Am I at risk of having a sudden cardiac arrest? | General | 3 | 12 | 183 | 3h |
| What are the next steps in assessing my risk? | ICD | 4 | 0 | 255 | 4h |
| Should my ejection faction (EF) be measured? | CPR | 3 | 0 | 8 | 7h |
| If my EF has been measured, should it be evaluated again for any change? | | 6 | 7 | 285 | 8h |
| Should I see a heart rhythm specialist to help determine my risk of SCA? | | 4 | 0 | 255 | 4h |
| If I am at risk of SCA, what are the treatment options? | | 4 | 0 | 255 | 4h |

FIG. 15

FIG. 29
120a
CHAT
Hey Mr. Snow. Looks like all your son's tests came back and they look good
Thanks Nurse Tyrell. That's great to hear. Do you think he can be discharged soon?
Yes. I'll have Dr. Stark confirm the discharge but I think it'll be today.
Thank you so much.

SYSTEMS AND METHODS FOR PROVIDING HEALTH INFORMATION

CROSS-REFERENCE TO RELATED APPLICATIONS

This application claims priority to U.S. patent application Ser. No. 17/064,864 filed Oct. 7, 2020, by inventors Krishna Bhimavarapu et al. and entitled SYSTEMS AND METHODS FOR PROVIDING HEALTH INFORMATION, which in turn claims priority to U.S. patent application Ser. No. 15/295,722 filed Oct. 17, 2016, by inventors Krishna Bhimavarapu et al. and entitled SYSTEMS AND METHODS FOR PROVIDING HEALTH INFORMATION, which in turn claims priority to U.S. provisional patent application Ser. No. 62/242,735 filed Oct. 16, 2015, by inventors Krishna Bhimavarapu et al. and entitled SYSTEMS AND METHODS FOR PROVIDING HEALTH INFORMATION, the complete disclosures of all of which are incorporated herein by reference.

BACKGROUND OF THE INVENTION

The present disclosure relates to systems and methods for providing health information regarding a patient's visit to a healthcare facility, such as a hospital.

SUMMARY

Some of the embodiments of the present disclosure address the past difficulties in presenting timely, helpful, and/or complete information to a patient, his or her friends or family, and other individuals associated with the patient before, during, and/or after the patient's visit to a healthcare facility. In one embodiment, a health information application adapted to be executed on an electronic device, such as, but not limited to, smart cell phone, a tablet, a laptop computer, or the like, is provided to a patient, his or her friends or family, and/or other individuals associated with the patient. The patient, or other receiver of the application, then utilizes the application on his or her smart cell phone or other electronic device. When utilized thereon, the electronic device retrieves a variety of different information about the patient's stay from one or more computer servers or software applications, some of which may be on the healthcare facility's local area network, and some of which may be coupled thereto via another network connection (e.g. the Internet). In other embodiments, a healthcare information application is provided that is accessed and used by healthcare providers in order to easily review and/or input information regarding patients, medical equipment, treatment, and other information.

According to one embodiment, a system is provided that includes a mobile electronic device adapted to perform the following: display on a display of the mobile electronic device first data regarding a patient's visit to a healthcare facility; process information indicating a current location of the mobile electronic device; and display second data regarding the patient's visit to the healthcare facility. The processor of the mobile electronic device delays displaying the second data until the mobile electronic device crosses a boundary of a geo-fenced area.

In some embodiments, the geo-fenced area encompasses the entire healthcare facility. In other embodiments, the geo-fenced area encompasses only a portion of the healthcare facility. In still other embodiments, multiple geo-fenced areas are defined and different data is delayed from being displayed depending upon which geo-fenced area is crossed.

The geo-fenced area or areas may have boundaries substantially defined by one of the following: a room within the healthcare facility, a floor within the healthcare facility, a wing within the healthcare facility, a department within the healthcare facility, a set of elevators within the healthcare facility, and a parking lot of the healthcare facility.

The mobile electronic device also displays, in at least one embodiment, third data regarding the patient's visit to the healthcare facility, wherein the processor of the mobile device delays displaying the third data until a clock in communication with the processor indicates a specific time has passed or a specific event has occurred. The specific time may correspond to a completion of a task in a treatment plan for the patient, and the specific event may include at least one of the following: admission to the healthcare facility; completion of a medical treatment within the medical facility; and discharge from the healthcare facility. In some embodiments, the specific event is a completion of a medical treatment and the mobile electronic device wirelessly receives a message indicating the completion of the medical treatment.

The mobile electronic device may also receive information from the patient and transmit the received information to a healthcare facility computer. In some embodiments, the received information includes answers provided by the patient to at least one question displayed on the display. The question relates to a quality of the patient's visit to the healthcare facility, in some embodiments. The question may be incorporated into a Hospital Consumer Assessment of Healthcare Providers and Systems (HCAHPS) score, in at least some embodiments. Such HCAHPS surveys were developed by the United States Department of Health and Human Services.

The second data displayed on the mobile electronic device relates, in some embodiments, to at least one of the following: a medication prescribed to the patient, a medical treatment scheduled for the patient, a location within the medical facility, a caregiver of the medical facility, dietary guidelines for the patient, and at least one question about a quality of the patient's visit to the healthcare facility.

In some embodiments, the mobile electronic device displays instructions enabling the user to authorize a family member to access third data regarding the patient's visit to the healthcare facility via a second mobile electronic device carried by the family member. The third data includes at least one piece of information recorded in an electronic medical record of the patient.

The mobile electronic device may also display instructions enabling the user to authorize a friend to access fourth data regarding the patient's visit to the healthcare facility via a second mobile electronic device carried by the friend.

In some embodiments, the mobile electronic device displays at least one control for controlling an aspect of a bed assigned to the patient and transmitting a command to the bed in response to the patient manipulating the control.

The mobile electronic device may also provide access to an electronic chat room that is limited to participants who have received treatment for a medical condition that is the same, or similar to, a medical condition of the patient. The electronic chat room may be limited to participants who have received treatment for the medical condition at the healthcare facility.

According to another embodiment, a system is provided that includes a mobile electronic device that is adapted to display first data regarding a patient's visit to a healthcare facility. The processor of the mobile electronic device is also adapted to display a sequence of patient events associated with the patient's visit to a healthcare facility, and to display further information regarding a selected one of the patient events in response to a user of the mobile electronic device selecting the selected patient event.

According to other aspects, the mobile electronic device communicates with an electronic medical records server at the healthcare facility in response to the user selecting the selected patient event.

The mobile electronic device may also, or alternatively, communicate with a bed server at the healthcare facility that receives status data from a plurality of beds. When communicating with the bed server, the device receives data from the bed server indicating how much time the patient has spent out of bed. The data from the bed server may also or alternatively include data indicating when the patient has returned to his or her bed.

According to another embodiment, a mobile electronic device is provided that is adapted to display on its display first data regarding a patient's visit to a healthcare facility. A processor of the mobile electronic device is also adapted to communicate with a bed server at the healthcare facility that receives status data from a plurality of beds. The mobile electronic device authorizes, based on user input, the automatic sending of a notification message to a second mobile electronic device associated with a friend or family member of the patient when the bed server receives status data from the patient's bed.

According to other aspects, the status data may indicate when the patient left his or her bed, returned to his or her bed, and/or when the patient is awake or asleep.

The mobile electronic device may also be configured to display questions regarding the patient's visit to the healthcare facility on the display of the first mobile electronic device, receive answers to the questions, and forward answers to the questions to a server located at the healthcare facility.

In some embodiments, the mobile electronic device, or a server in communication with the mobile electronic device, is adapted to receive a code from an electronic medical records server at the healthcare facility, convert the code to a description of the service, and display the description of the service on the screen of the first mobile electronic device. The code may be an International Classification of Disease (ICD) code, or other code commonly used in healthcare settings for documenting medical tasks.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 15 is an illustrative example of a screen shot displayable on the mobile electronic device showing a list of discussion topics of an electronic chatroom accessible to the patient;

DETAILED DESCRIPTION OF THE EMBODIMENTS

Figure 1:
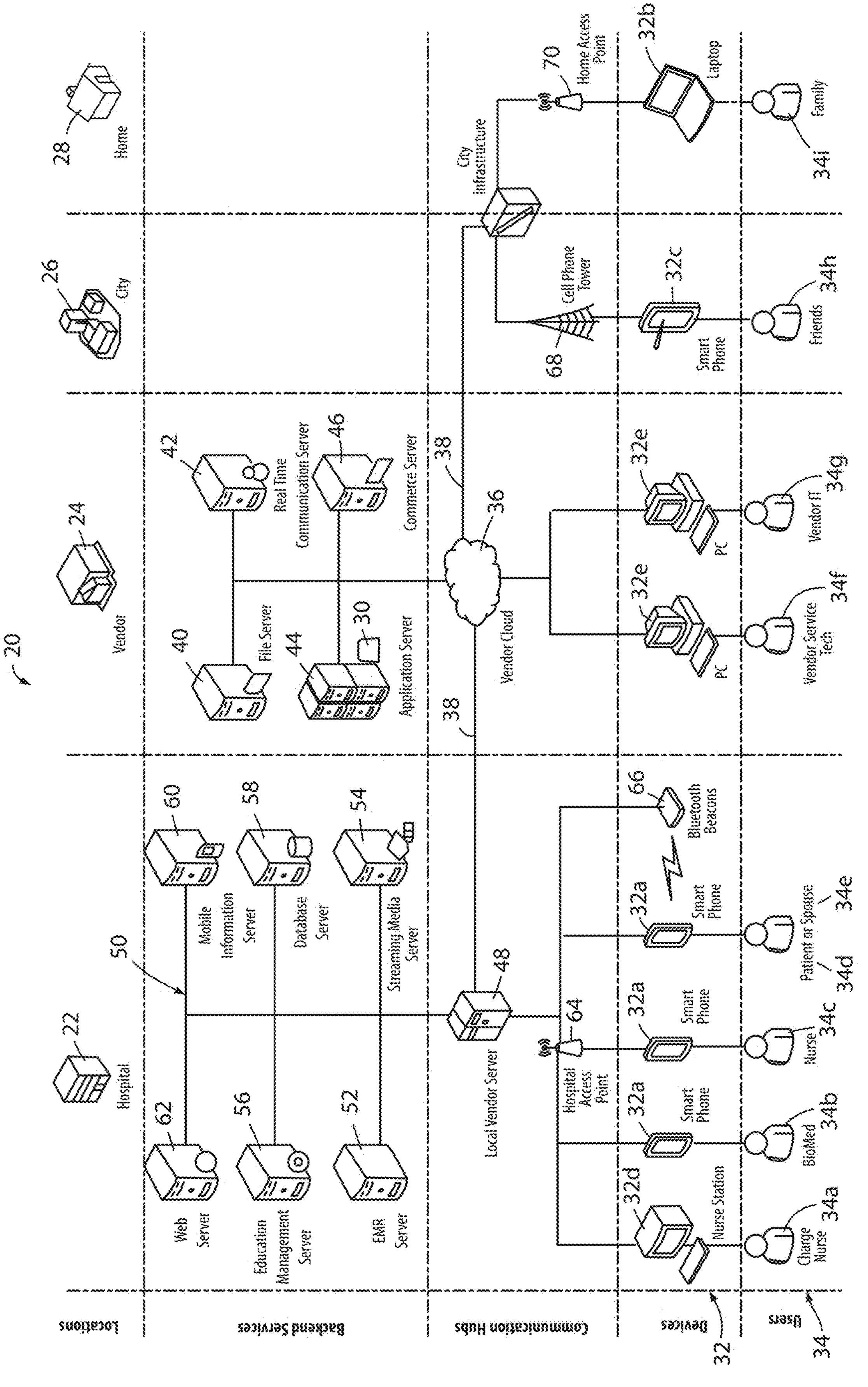
FIG. 1 is a block diagram of a first embodiment of a health information system according to the present disclosure.

A health information system 20 according to a first embodiment of the disclosure is shown in FIG. 1. Health information system 20 of FIG. 1 spans a set of geographic locations that includes at least one hospital 22, a place of business of a vendor 24, an area outside of the hospital 22, such as a city 26, and one or more homes 28. In different embodiments, the geographic extent of health information system 20 may be changed, including consolidating one or more of the resources at the vendor 24's place of business within hospital 22 and/or elsewhere. In still other embodiments, health information system 20 is adapted to operate without extending to city 26 and/or homes 28. In still other embodiments, still other modifications to the geographical span of health information system 20 may be made.

Health information system 20 of FIG. 1 includes at least one health information software application 30 (hereinafter referred to as "health info app 30") that is supplied to one or more electronic devices 32 of one or more users 34. As shown by way of illustration in FIG. 1, the electronic devices 32 include mobile electronic devices, such as smart phones 32*a*, laptops 32*b*, and/or tablets 32*c*, as well as generally stationary electronic devices, such as nurse station computers 32*d* and/or personal computers (PCs) 32*e*. When implemented on a smart phone 32*a*, the smart phone 32*a* may utilize an Android operating system or an Apple IOS operating system. In still other embodiments, device 32 utilizes another type of operating system besides Android and iOS (such as, but not limited to, Firefox OS, Sailfish OS, Windows Phone, Blackberry, Tizen, and others). Still further, in some embodiments, health info app 30 is a web-based application that is accessed by utilizing a conventional web browser, such as, but not limited to, Internet Explorer, Internet Edge, Firefox, and/or Apple Safari.

The users 34 of health info app 30 may vary, and include such users as charge nurses 34*a*, biomedical technicians 34*b*, nurses or other caregivers 34*c*, patients 34*d*, patient spouses 34*e*, service technicians 34*f* of the vendor 24, Information Technology (IT) personnel 34*g* of the vendor 24, friends 34*h* of patients 34*d*, and family 34*i* of patient 34*d*.

Health info app 30 is supplied, in the embodiment illustrated, from a cloud location 36 of vendor 24. Cloud location 36 need not be owned by or operated by vendor 24, but instead provides a location accessible to the Internet for distributing health info app 30 to Internet-connected users and allowing one or more resources at vendor 24's place of business to communicate with health info app 30. As shown by way of illustration in FIG. 1, cloud location 36 includes an Internet connection 38 that enables vendor 24 to forward health info app 30 to hospital 22, city 26, and one or more homes 28. Cloud location 36 also provides a communication conduit for health info app 30, after installation on one or more electronic devices 32, to communicate with the resources of vendor 24.

These vendor resources include a file server 40, a real time communication server 42, an application server 44 and a commerce server 46. It will be understood that this particular set of resources may vary and that vendor 24 may include a different set of resources, including, but not limited to, connections to resources provided by third parties with which vendor 24 has one or more contractual agreements for providing support and/or services to health info app 30. File server 40 stores files and data used by health info app 30. Real time communication server 42 manages the ongoing communications between the resources of vendor 24 and the multiple devices 32 that have health info app 30 stored and executing thereon. Application server 44 provides the health info app 30 that is initially downloaded onto the devices 32, as well as overseeing updates to health info app 30 and other operational aspects of health info app 30. Commerce server 46 manages the billing and financial information associated with the use of health info app. In some instances, this billing is directed to hospitals 22 which provide health info app 30 to one or more of their patients and/or the friends and relatives of the patients. In some instances, commerce server 46 may oversee financial charges that are applied directly to one or more users 34 of health info app 30.

After health info app 30 is downloaded to a hospital 22 via Internet connection 38, it is initially stored on a local vendor server 48. Local vendor server 48 is supplied by vendor 24. Local vendor server 48 is, in some embodiments, purely a software server 48 that resides on server hardware owned and/or operated by hospital 22. In other embodiments, vendor 24 may provide server hardware for local vendor server 48. Local vendor server 48 oversees the distribution of individual copies of health info app 30 to the devices 32 located within hospital 22, as well as the communication between those devices 32. Local vendor server 48 also provides an interface between the devices 32 within hospital 22 and vendor cloud 36. Still further, local vendor server 48 provides an interface between devices 32 and one or more servers or services that are a part of a local area network 50 of hospital 22.

In the embodiment shown in FIG. 1, local area network 50 of hospital 22 includes an electronic medical records (EMR) server 52, a streaming media server 54, an education management server 56, a database server 58, a mobile information server 60, and a web server 62. It will be understood that these particular servers are but one illustration of the makeup of an illustrative hospital network 50. The specific number and type of servers that may be present in a given hospital 22 will vary from hospital to hospital, depending upon the computer architecture of a given healthcare facility, as well as the types of servers and/or software applications that are operating on the hospital's network 50. Local vendor server 48 may therefore communicate with different numbers, types, and/or combinations of the servers illustratively shown in FIG. 1.

Local vendor server 48, in at least one embodiment, communicates with electronic devices 32 via one or more wireless access points 64 of computer network 50 of a hospital 22. In at least one embodiment, such wireless communication is carried out via WiFi (IEEE 802.11). Other wireless protocols and/or wired protocols can alternatively be used, including combinations of such protocols (such as, but not limited to, both WiFi and Ethernet). One or more of the electronic devices 32 may also be adapted to communicate with a Bluetooth (IEEE 802.15.1) beacon 66 that is communicatively coupled to local network 50. Such devices 32 are therefore able to communicate with local vendor server 48 via Bluetooth communications, and vice versa.

Local vendor server 48 also communicates with one or more of the servers 52-62 on network 50. EMR server 52 is an electronic medical records server that stores, retrieves, and updates medical records of the patients at hospital 22. Streaming media server 54 is a server that provides streaming video, audio, and/or other content when requested by the health info apps 30 operating on any of the devices 32 of any of the users 34, as will be discussed in greater detail below. Education management server 56 provides educational materials regarding health conditions, drugs, treatments, and the like. These materials are accessed and displayed by health info app 30 when such information is requested by a user 34.

Database server 58 contains data used by health info app 30 at different times, including, but not limited to, map information regarding hospital 22, employees and personnel of hospital 22, work flow information, and other data. Mobile information server 60 manages communications between healthcare personnel, such as one or more smart phones 32*a*, badges, pagers, etc. Thus, for example, if a particular caregiver, or set of caregivers, is to be notified of an alert, or provided with other information, health info app 30 can send a notification request via local vendor server 48 to mobile information server 60 and mobile information server 60 will send a text, page, or other notification to a mobile device carried by the caregiver, or set of caregivers. Web server 62 provides web access to any of the servers and/or applications executing on network 50 and/or in communication with network 50. Health info app 30 is therefore able to utilize web server 62 to communicate with the World Wide Web using web server 62.

All of the servers 52-62 may be conventional servers. Health info app 30 is configured to extract the information contained within any one or more of these servers 52-52 as needed by app 30, and in some cases update the information stored therein, as will be described in greater detail below. Health info app 30 may be configured to communicate with additional servers not shown in FIG. 1 and/or with different combinations of servers. Still further, in some embodiments, the data contained within any of servers 52-62 may be located off site of hospital 22. In such embodiments, local vendor server 48 provides the information contained within the server by communicating through web server 62 and/or Internet connection 38 with the offsite servers.

The Bluetooth beacons 66 located at hospital 22 may be part of a location system in which the locations of each of the Bluetooth beacons 66 are fixed and known to server 48. When local vendor server 48 receives a message from a device 32 that passes through a Bluetooth beacon, the Bluetooth beacon appends to the message a unique identification corresponding to that particular Bluetooth beacon 66. Local vendor server 48 consults a look-up table that correlates that unique identifications it receives from the Bluetooth beacons 66 to their locations within the hospital 22 (such a table may be stored in database server 58, or elsewhere). Local vendor server 48 is therefore able to determine the approximate location of any device 32 that is communicating with local vendor server 46 via a Bluetooth beacon 66. In other words, the location of that device is determined to be within a close proximity of the Bluetooth beacon 66, given the relatively short range of Bluetooth. Similarly location technology may be used for determining the location of devices communicating via WiFi access points 64 using knowledge of the location of the access point 64 and, in some cases, triangulation of signal strength. One example of such location technology that may be used with health info app 30 is disclosed in commonly assigned U.S. patent application Ser. No. 14/559,458 filed Dec. 3, 2014, by inventors Michael Hayes et al. and entitled PATIENT SUPPORT APPARATUS COMMUNICATION SYSTEMS, the complete disclosure of which is incorporated herein by reference.

In other embodiments, a conventional RF ID tag system may be used for detecting the location of mobile electronic devices 32. In still other embodiments, the location of mobile electronic devices 32 can be monitored using any of the locating techniques disclosed in commonly assigned U.S. Pat. No. 8,674,826 issued to Becker et al. and entitled LOCATION DETECTION SYSTEM FOR A DEVICE, the complete disclosure of which is hereby incorporated herein by reference. Still further, in some embodiments, when health info app 30 is installed on a smart phone 32*a*, it uses the built-in location technologies of the smart phone 32*a* (GPS, cellular triangulation, etc.) to determine its location, which is then forwarded to local vendor server 48.

Access points 64 and beacons 66 contained with hospital 22 enable users of health info app 30 to communicate with vendor cloud 36 while those users are at hospital 22. As will be discussed in greater detail below, however, not all users of health info app 30 are located within hospital 22. Some users are located outside of hospital 22, such as in city 26. It will be understood that references to "city 26" refer to not just the local municipality in which hospital 22 is located, but instead refers to a broader geographic designation that includes any areas in which potential patients and/or relatives of patients of hospital 22 may be located. Thus, in some embodiments, "city 26" is broad enough to include any place outside of hospital 22 in which there is Internet access.

Users 34 who are located outside of hospital 22 and in city 26 are able to communicate with vendor cloud 36 via one or more cell phone towers 68 that provide Internet access to mobile phone subscribers. As indicated in FIG. 1, such users may be friends 34*h* of a patient at hospital 22, although such cellular communication is not limited to only friends 34*h*. Further, it will also be understood that communication with vendor cloud 36 is not limited to cellular communications. Thus, for example, users 34 located within city 26 may communicate with vendor cloud 36 using alternative means, such as, but not limited to, public WiFi access points, public wired Internet connections, and the like.

Users 34 may also be located within individual homes 28. Such users may communicate with vendor cloud 36 using a home based access point 70, although it will be understood that alternative methods for communicating with vendor cloud 36 are possible. Any conventional home-based Internet connection, such as WiFi, Digital Subscriber Lines (DSL), fiber optic connections, satellite connections, cellular connections, etc. may be used by home based users to communicate with vendor cloud 36.

Vendor cloud 36 allows and manages the communications between users 34 of health info app 30 who are located outside of hospital 22 and the data located at hospital 22. In some cases, vendor cloud 36 allows communication between the health info app 30 used by patient 34*d* at the hospital and the health info app 30 installed on those user's electronic device 32. Vendor cloud 36 manages access rights to health information so that only authorized friends of a specific patient 34*d* are allowed to use health info app 30 to see information regarding that specific patient 34*d*. In other words, the information that is displayable by health info app 30 is not open to the public. Further, the health information of a first patient 34*d* is only viewable by authorized friends and relatives of that first patient, and not other members of the public who may have health info app 30 installed on their device 32. Thus, for example, if there are two patients at hospital 22 and the first patient has a first set of friends and family and the second patient has a second set of friends and family, the first set of friends and family will only be able to access information about the first patient using health info app 30, not information about the second patient. Similarly, the second set of friends and family will only be able to access information about the second patient using health info app 30, not information about the first patient.

Vendor 24 may also have one or more copies of health info app 30 operating on one or more devices 32 that are directly coupled to vendor cloud 36. Such users include one or more Information Technology (IT) persons 34*g* who are able to actively manage the operation of health info app 30, troubleshoot health info app 30, and access information regarding the operation of health info app. Vendor 24 may also include one or more service technicians 34*f* who use health info app 30 for scheduling, monitoring, and carrying out the servicing of one or more medical devices used by hospital 22.

Although FIG. 1 illustrates a single hospital 22, it will be understood that this is merely for purposes of illustration. In alternative embodiments of health information system 20, multiple hospitals 22 are coupled to vendor cloud 36, each of which includes a local vendor server 48 that manages communications between the vendor cloud 36 and that particular hospital 22. Further, it will be understood that health info app 30 is not limited to be used only at hospitals 22, but instead may be used at other healthcare facilities, nursing homes, clinics, treatment facilities, and/or other locations. Still further, health info app 30 is, in some embodiments, a thin client app that runs thinly on the device 32 with most of its computations done remotely at either local vendor server 48 and/or one or more computing resources located at vendor 24. In other embodiments, health info app 30 is a thick client app that runs thickly on device 32 and utilizes local vendor server 48 and/or the resources of vendor 24 primarily for accessing data it does not have local access to and/or for communications.

Health info app 30 is configured in one embodiment to provide timely and contextual information regarding one or more aspects of a patient's visit to hospital 22. These features are discussed in more detail below but generally include information regarding arrival at the hospital (e.g. parking, location, check-in, etc.), the patient's expected treatment and procedures, the patient's schedule, milestones achieved by the patient, maps of locations within the hospital 22, general medical information, providing feedback to the hospital 22 regarding the patient's visit, and follow-up information for after the patient's discharge from the hospital 22. In other embodiments, health info app 30 is also configured to provide information used for managing one or more pieces of medical equipment at the hospital 22. In these embodiments, the equipment management features may be combined together with the patient information features of health info app 30, or they may be included in a separate health info app 30 that is only accessible to authorized users who have need for such equipment management information. If the patient information features and equipment management features are combined into a single health info app 30, then health info app 30 is configured to limit usage of the equipment management features to only personnel having need for that information, and to likewise limit usage of the patient information features to only people who are authorized to access such information.

Figure 2:
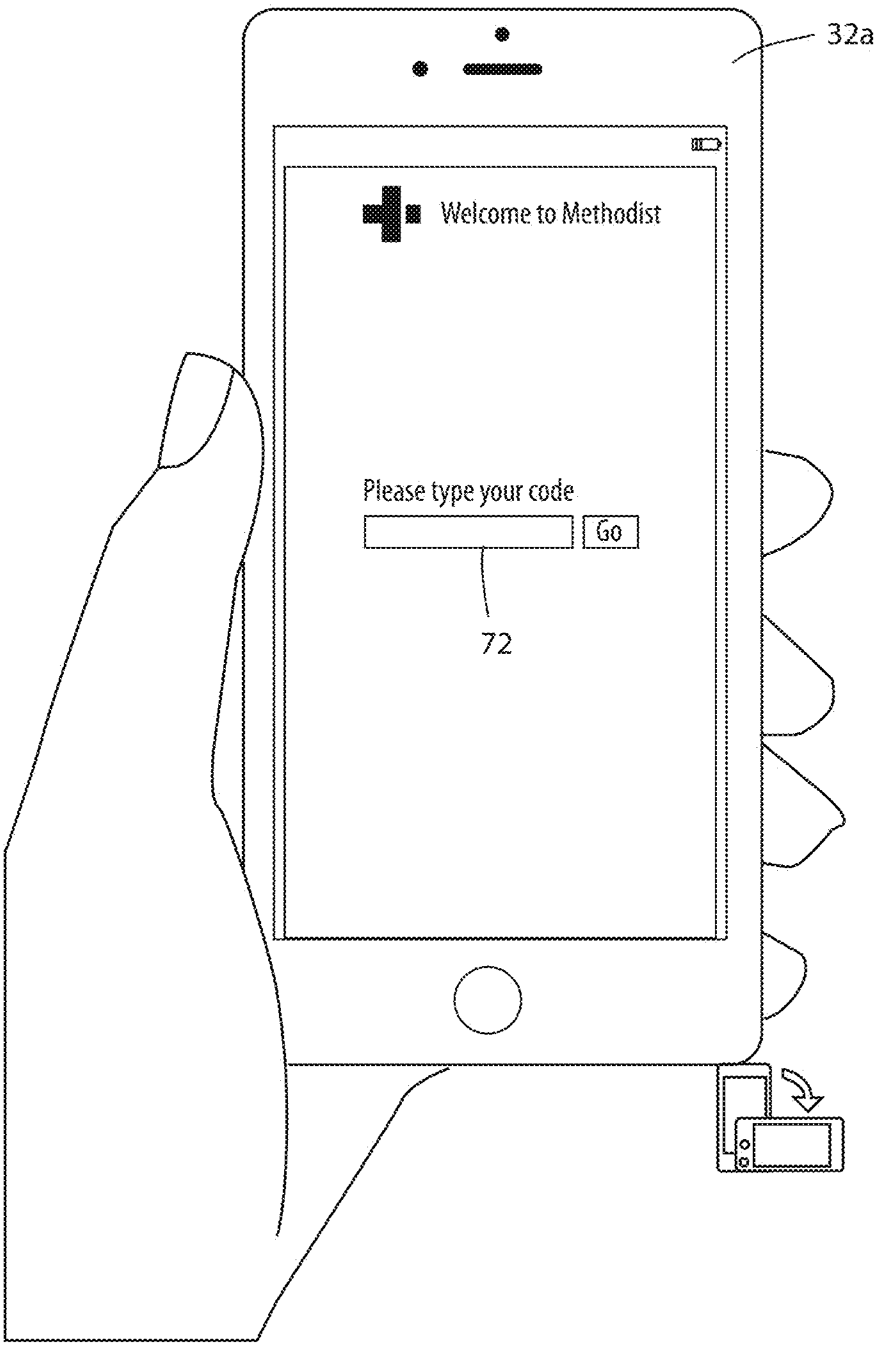
FIG. 2 is an elevation view of an illustrative mobile electronic device incorporating a healthcare application of the health information system.

FIG. 2 illustrates one manner of allowing a user 34 to gain access to and/or install health info app 30. That is, a user may navigate to a particular web-page, or other Internet location, using his or her device 32. When arriving at that web-page, or other location, the user is prompted for a code that is entered into a code field 72. When an authorized code field is entered in field 72, the user is able to install health info app 30 on his or her device 32. The list of authorized codes is maintained at vendor cloud 36 and/or at local vendor server 48. Hospital 22 and/or vendor 24 distribute these codes to patients 34*d* and other authorized users 34 in cooperation with each other. In some embodiments, one or more additional codes are provided to a patient 34*d* who is given permission to share those additional codes with people of his or her choosing, such as family members, friends, or other individuals.

In some embodiments, hospitals 22 may encourage the use of health info app 30 by providing a bar code or QR code at various locations within hospital 22. After scanning the bar code or QR code, the user is taken to the download screen, such as shown in FIG. 2. In some embodiments, hospital 22 may provide patients 34*d* with a device 32*a*, 32*c*, or the like, that has health info app 30 pre-loaded on it. Hospitals 22 may also advise and/or remind the patients 34*d* to download health info app 30 upon check in. The code for a particular patient 34*d* may be provided at check in, sent to the patient's device 32 prior to check in (email, text, etc.), sent via conventional postal mail, or delivered in other manners.

As noted, vendor 24 and hospital 22 cooperate and share information regarding what codes have been provided to users 34. In this manner, when a particular hospital 22 provides a code to a particular patient 34*d*, vendor 24 is apprised of this fact so that communications received at vendor cloud 36 from sources outside of the that hospital 22 (e.g. city 26 and/or home 28) are routed to the proper hospital 22. Vendor 24 and hospital 22 may also agree that the codes provided to user 34 expire after certain time periods so that health info app 30 may no longer provide health information after those time periods expire. The time periods may vary for different users 34, the individual schedule and/or treatment of particular patients, and/or based on other factors. In some embodiments, after the time period has expired, a potential user 34 who has not downloaded health info app 30 is no longer able to do so. Further, in some embodiments, users 34 who have already downloaded health info app 30 are no longer able to use some or all of the features of health info app 30 after the appropriate time period has expired.

After a user 34 has entered an approved code into code field 72, health info app 30 is downloaded and installed on that user's device 32. The downloaded health info app 30 comes from vendor 24, who may store health info app 30 on application server 44. In some embodiments, vendor 24 allows one or more copies of health info app 30 to be stored at local vendor server 48 so that health info app 30 may be downloaded to devices within hospital 22 without requiring access to vendor 24. This enables health info app 30 to be installed when communications with vendor cloud 36 may be temporarily interrupted. In still other embodiments, health info app 30 may be downloaded from one or more commercially available app stores, such as, but not limited to, the Apple iTunes store or Google Play store. When downloaded from these commercial stores, the user may need to enter the code prior to installation of health info app 30 or it may be entered after download and installation of health info app 30. In some embodiments, a first code may need to be entered for downloading and a second code may need to be entered for using health info app 30. Other variations are possible.

Figure 3:
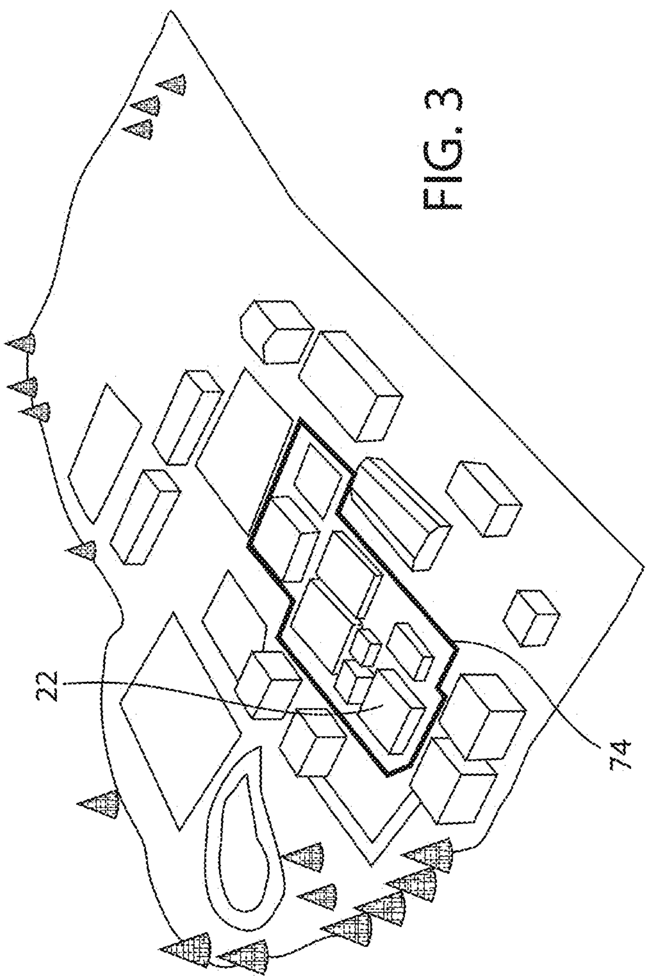
FIG. 3 is a perspective view of an arbitrary healthcare facility having a geo-fenced area that, when crossed, triggers an action by the health information application.

Once health info app 30 is installed on a particular device, health info app 30 is configured to tailor many of the features and information provided to the user 34 based upon the user's location. As shown in FIG. 3, health info app 30 uses geofencing to determine one or more features to activate and/or data to display or make available. FIG. 3 illustrates a geo-fenced area 74 of an arbitrary hospital 22. The boundaries of geo-fenced area 74 may vary (including, but not limited to, geofenced areas as small as an individual bay of a multi-tenant hospital room), and multiple geo-fenced areas 74 of different sizes and/or shapes may be included for a single hospital 22.

Health info app 30 uses the geo-fenced areas 74 in conjunction with location information provided by device 32 (e.g. the location services of a smart phone 32*a*) and/or the location information provided from a hospital's location system (e.g. beacons 66 and/or any of the location techniques previously described). Health info app 30 uses this location information to detect when a user 34 crosses one of the boundaries of geo-fenced area 74. As will be described in more detail below, health info app 30 is configured in some embodiments to take one or more appropriate actions in response to such boundary crossings. In one embodiment, health info app 30 provides info to a user 34 that wasn't previously provided to the user prior to the user crossing the geo-fenced area. As one example, health info app 30 provides directions to the user 34 of app 30 regarding where to park, enter, and/or walk within the hospital 2 when the user crosses a geo-fenced area that encompasses the hospital 22.

Figure 4:
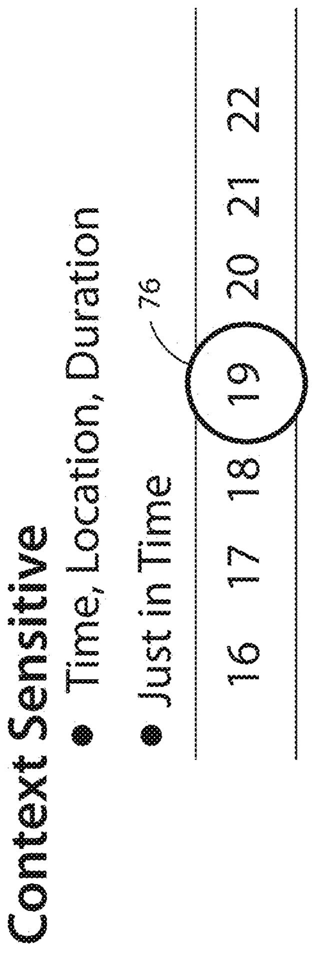
FIG. 4 is a diagram indicating the time sensitivity of the health information application.

In addition to displaying location-sensitive information and/or providing location-sensitive features, health info app 30 is also configured to display time-sensitive information and/or provide time-sensitive features. As shown in FIG. 4, health info app 30 uses the current date 76 (the $19^{th}$ day of the month) and/or time to display data and/or provide different features, as will be discussed in greater detail below. In some embodiments, for example, health info app 30 compares the current time and/or date to one or more events on a time line of the patient's care and takes action according to the proximity of the events to the current time and/or date. For example, if a patient is scheduled for a medical treatment on a specific date and the treatment requires the patient to fast for so many hours prior to the treatment, health info app 30 is adapted to send a reminder to the patient (e.g. a text, email, or the like), or otherwise issue a reminder alert (by sound, vibrations, illuminating one or more lights, etc.) when the time for fasting arrives (and/or at a predetermined amount of time prior to its arrival). Other time sensitive reminders, information displays, and/or feature provisions are of course also possible.

Figure 5:
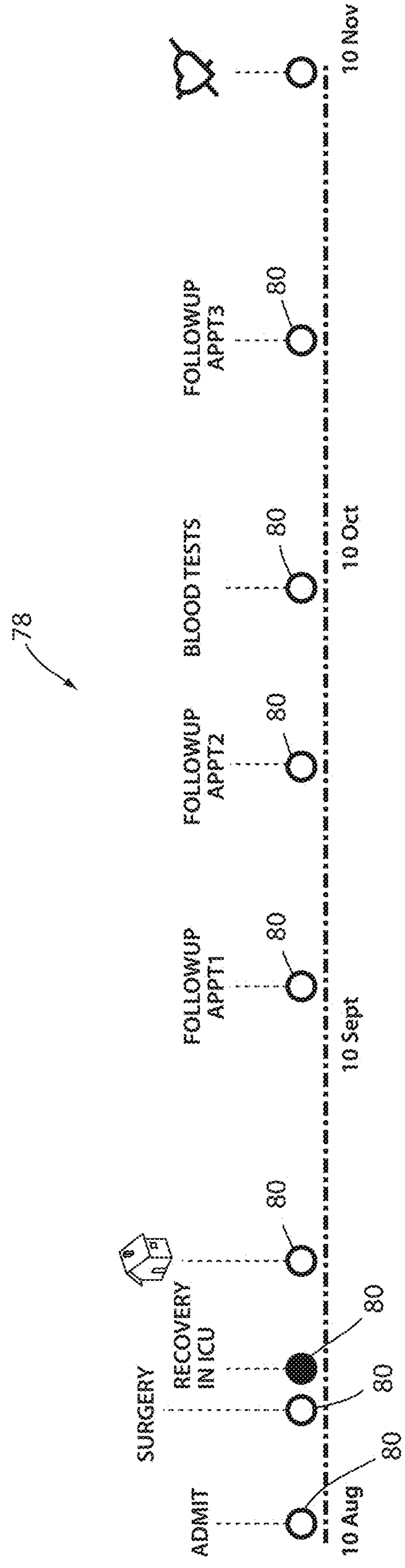
FIG. 5 is a diagram of an illustrative set of events regarding a patient's scheduled healthcare facility visit that may be displayed and/or used by the health information application.

FIG. 5 illustrates a timeline 78 of an arbitrary example of a patient's schedule with respect to a particular hospital and/or treatment plan. Timeline 78 identifies one or more events 80 that are scheduled to occur for a particular patient. Timeline 78 is displayable to users 34 of health info app 30. The information in timeline 78 is communicated to health info app 30 from EMR server 52 and/or from any other servers maintained at hospital 22 that contain this information. In addition to displaying timeline 78, health info app 30 is configured to provide reminders, locations, and directions associated with each of the events 80. Thus, health info app

30 allows a user to select any of the events 80 to receive more information about the event 80, including, but not limited to, the content, time, and/or location of the event, and directions to the event. Health info app 30 displays this information in response to the user's selection of a particular event 80. It will be understood that the term "selecting" as used herein includes not only clicking or double clicking with a computer mouse, but also touching the area of a touchscreen display that corresponds to the location of the selected event 80, and/or any other known methods for choosing an item displayed on a screen of an electronic device 32.

Figure 6:
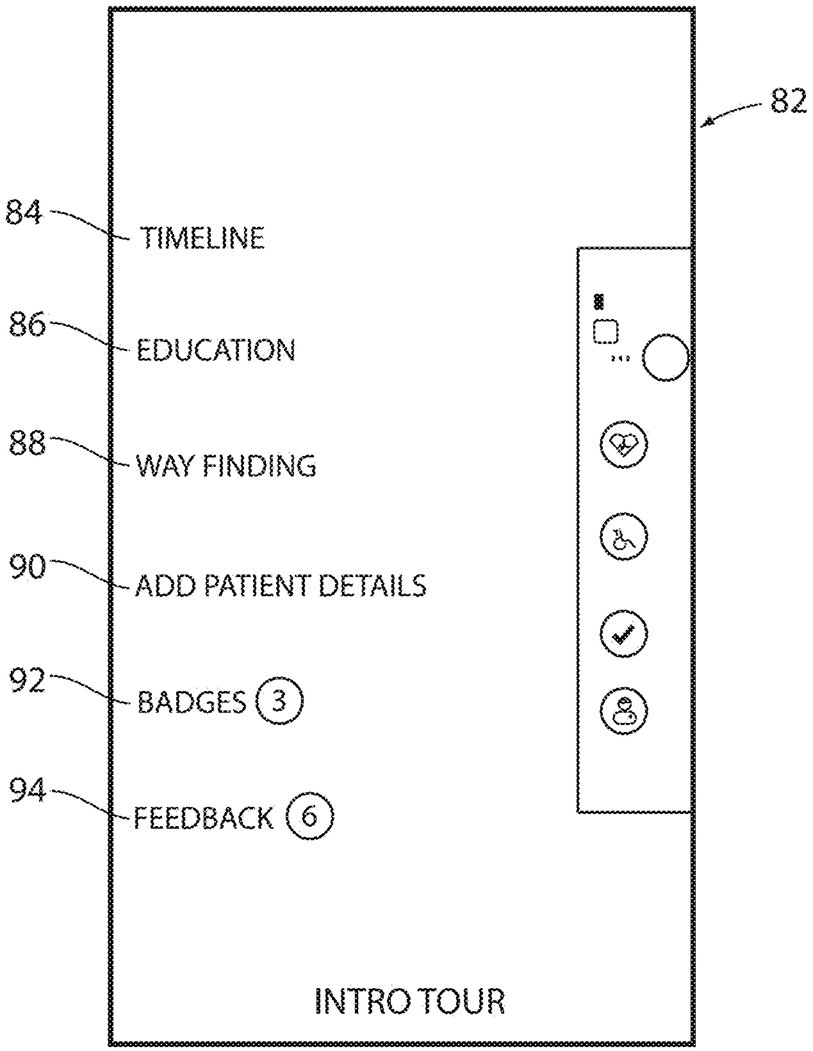
FIG. 6 is an illustrative example of a screen shot displayable on the mobile electronic device showing a menu for the health information application.
Figure 20:
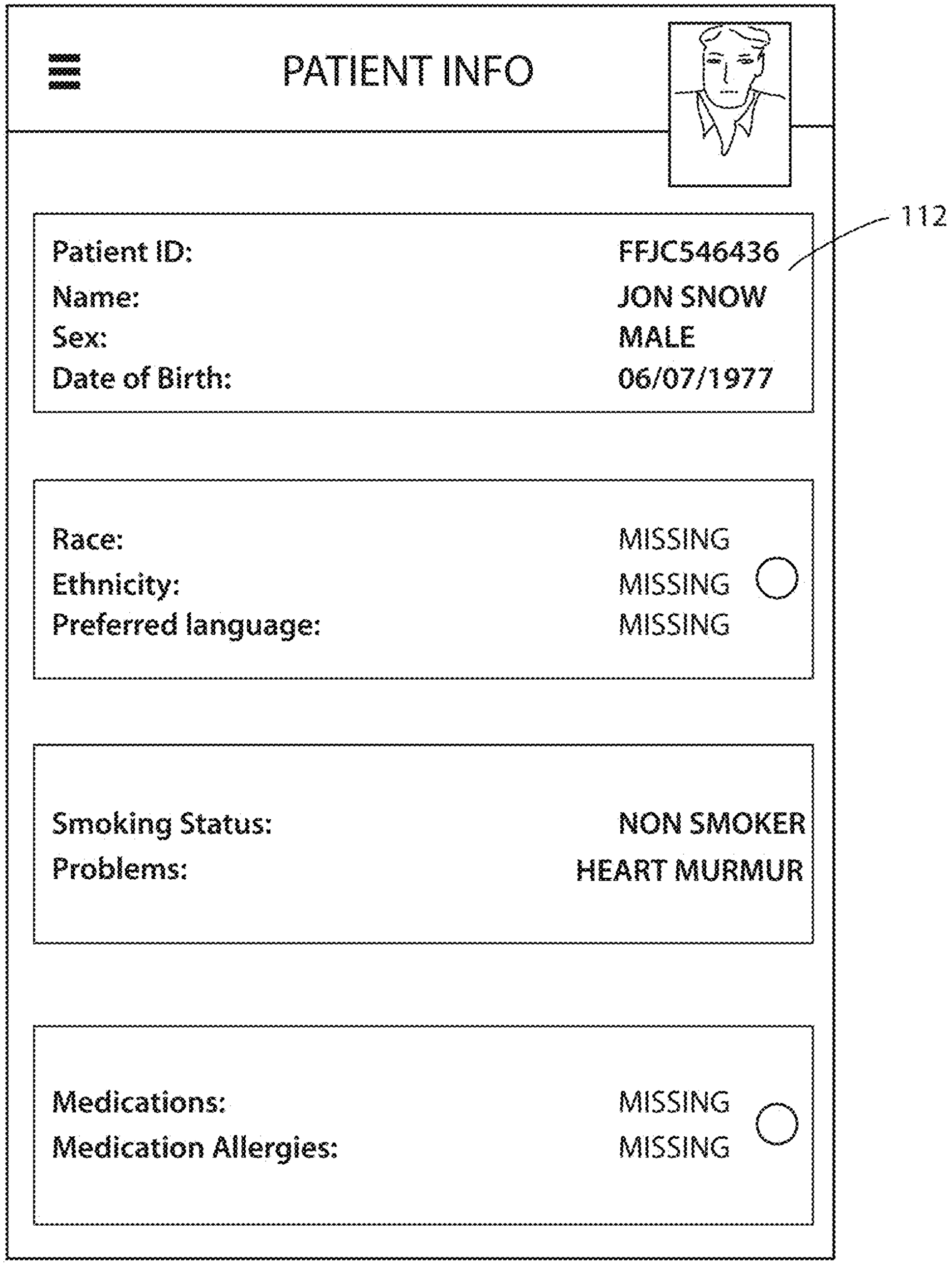
FIG. 20 is an illustrative example of a screen shot displayable on the mobile electronic device showing patient information accessible to, and editable by, authorized friends and/or relatives of the patient.

FIG. 6 illustrates one example of a main menu screen 82 that health info app 30 displays on the device 32 on which it has been installed. Main menu screen 82 includes a plurality of menu options that a user may select. These include, but are not limited to, a timeline option 84, an education option 86, a way finding option 88, a patient information option 90, a badge option 92, and a feedback option 94. Examples of screens displayable by health info app 30 in response to selecting timeline option 84 are shown in FIGS. 7-13. Examples of screens displayable by health info app 30 in response to selecting education option 86 are shown in FIGS. 14-15. Examples of screens displayable by health info app 30 in response to selecting way finding option 88 are shown in FIGS. 16-19. An example of a screen displayable by health info app 30 in response to selecting patient information option 90 is shown in FIG. 20. Examples of screens displayable by health info app 30 in response to selecting badge option 92 are shown in FIGS. 21-24. Examples of screens displayable by health info app 30 in response to selecting feedback option 94 are shown in FIGS. 25-28.

It will be understood by those skilled in the art that the particular set of options shown on main menu screen 82 may be changed from what is illustrated in FIG. 6. Additional and/or fewer options are included in some embodiments. In some embodiments, the options presented by health info app 30 vary based upon the particular user 34 of app 30 with some users being prevented from accessing one or more options. Still further, in some embodiments, the set of menu items shown on screen 82 changes in response to the current time and/or the location of the user 34.

Figure 7:
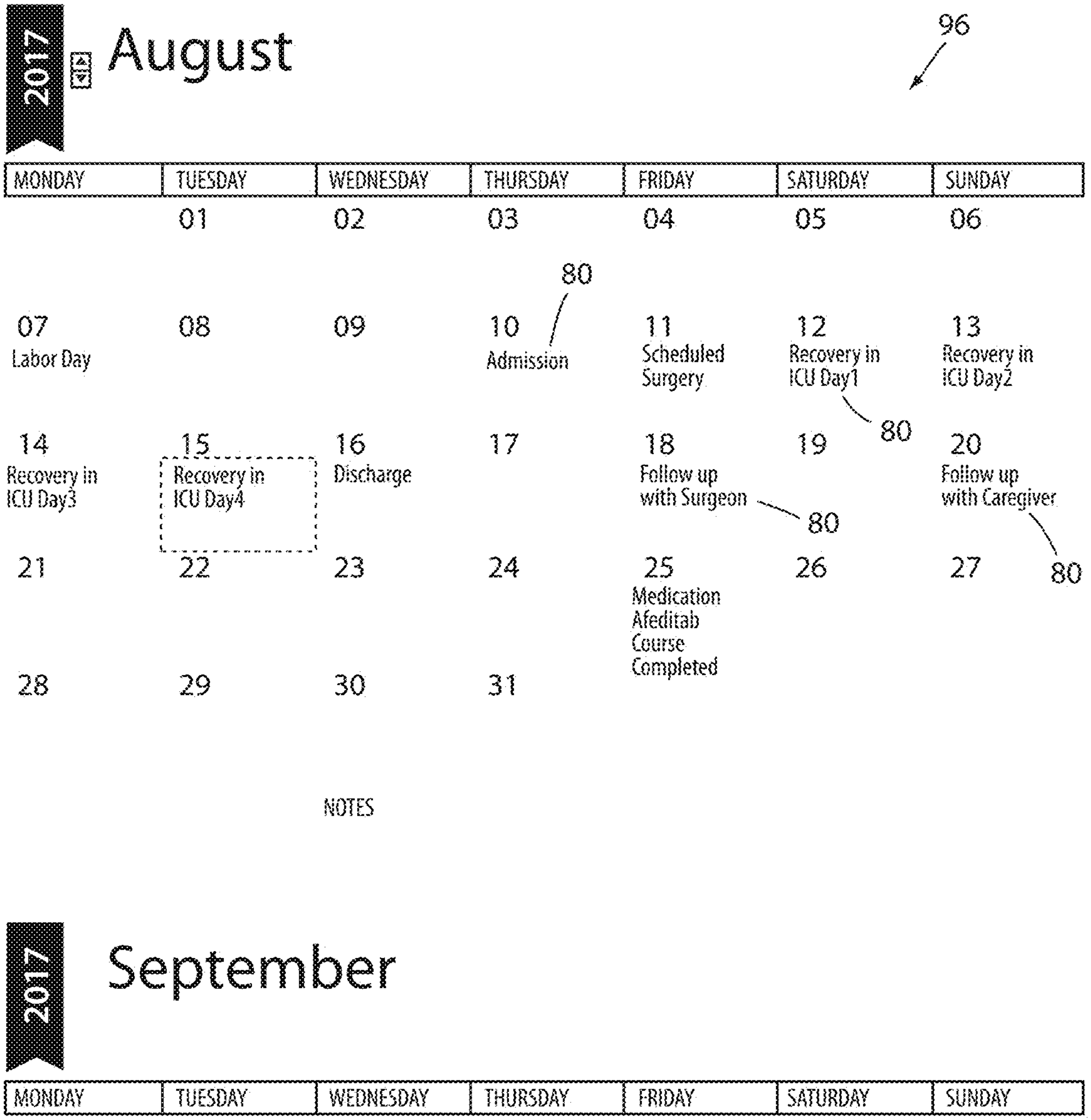
FIG. 7 is an illustrative example of a screen shot displayable on the mobile electronic device showing information related to a patient's hospital visit integrated into a calendar.
Figure 8:
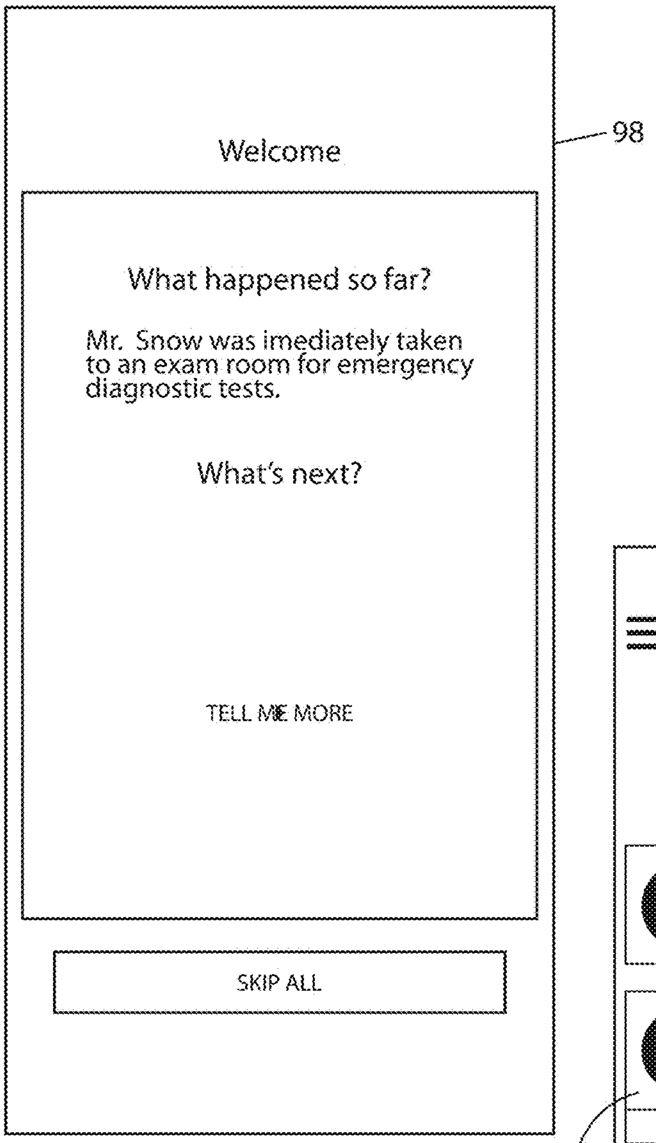
FIG. 8 is an illustrative example of a screen shot displayable on the mobile electronic device showing event information regarding the patient's hospital visit.

As noted, FIGS. 7-13 illustrate a plurality of screens that are displayable by health info app 30 in response to a user selecting timeline option 84 on screen 82. FIG. 7 shows a calendar screen 96 in which the patient's timeline 78 is shown on a calendar. In some embodiments, health info app 30 is configured to automatically integrate the events 80 of timeline 78 into a conventional calendar program that is also executing on the user's device 32 (e.g. a Microsoft Outlook calendar, Google calendar, Apple calendar, etc.). In this manner, the user 34 may use all of the reminder features (and other features) of their preferred calendar program with the events 80 of timeline 78.

In some embodiments of health info app 30, when health info app 30 is downloaded on a device 32 other than the patient 34*d*'s device, health info app 30 is configured to populate the calendar with an identification of the patient 34*d* so that the user of that device understands who the calendar entries relate to. Such patient identification is not provided, in some embodiments, by the copy of health info app 30 that is executing on the patient's device because the patient already knows that the events 80 on his or her calendar relate to himself or herself.

Figure 9:
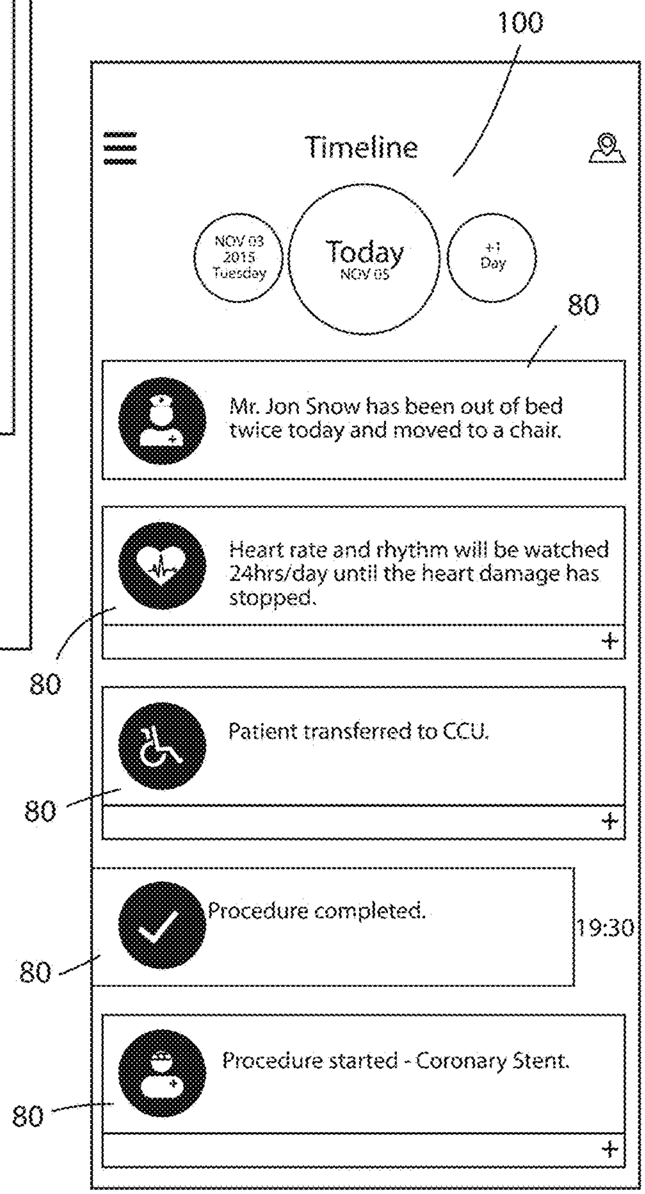
FIG. 9 is an illustrative example of a screen shot displayable on the mobile electronic device showing a more detailed listing of event information regarding the patient's hospital visit.

FIG. 9 illustrates a summary screen 98 that summarizes all of the events that have occurred so far with respect to patient 34*d*. These events include not only the events 80 scheduled on timeline 78, but any events that have occurred that were not on timeline 78. Summary screen 98 is displayed, in some embodiments, the first time a user 34 selects timeline option 84 from menu screen 82 (FIG. 6). When the user subsequently selects timeline option 84, health info app 30 displays a different screen, such as the screen shown in FIG. 9.

The summary screen 98, as well as the other screens shown in FIGS. 9-13, are populated with content based upon communications between health info app 30 and EMR server 52. That is, health info app 30 retrieves events 80 and information regarding those events from EMR server 52. In addition, health info app 30 is configured to allow on or more caregivers to use their own copies of health info app 30 to input data regarding one or more events 80 of patients 34*d* under their care. As a result, the timeline screens shown in FIG. 9-13 may include content that is provided from the caregivers associated with a patient that is sent from the devices 32 of those caregivers to local vendor server 48, which then forwards the information to the health info apps 30 executing on the devices 32 that are authorized to receive data for those particular patients. Still further, in some embodiments, health info app 30 retrieves information for populating the screens of FIGS. 9-13 from one or more other servers in communication with network 50.

In some embodiments, health info app 30, or a server in communication with health info app 30 (e.g. local vendor server 48), reads medical codes from EMR server 52 and translates the codes into a written description that is understandable to people who are not medical coders. For example, an ICD code ICD-9-CM might be translated to "administered diphtheria immunization." Health info app 30, or a server in communication therewith, is configured in some embodiments to convert codes from different coding systems, such as ICD, HCPCS, CPT, ICF, DRG, and/or NDC into written descriptions that are understandable by untrained users 34 of health info app 30.

FIG. 9 illustrates a day listing screen 100 that lists one or more event 80 that have occurred, or are scheduled to occur, on a particular day. In the example shown in FIG. 9, there are five events 80 listed for November 5, which is an arbitrarily selected day. If a user 34 selects one of the events 80 shown on day listing screen 100, additional information is retrieved by health info app 30, if available. Such additional information may include links to documentation, forms, reminders, appointments, staff information, and/or any other information relevant to the particular event 80.

Figure 10:
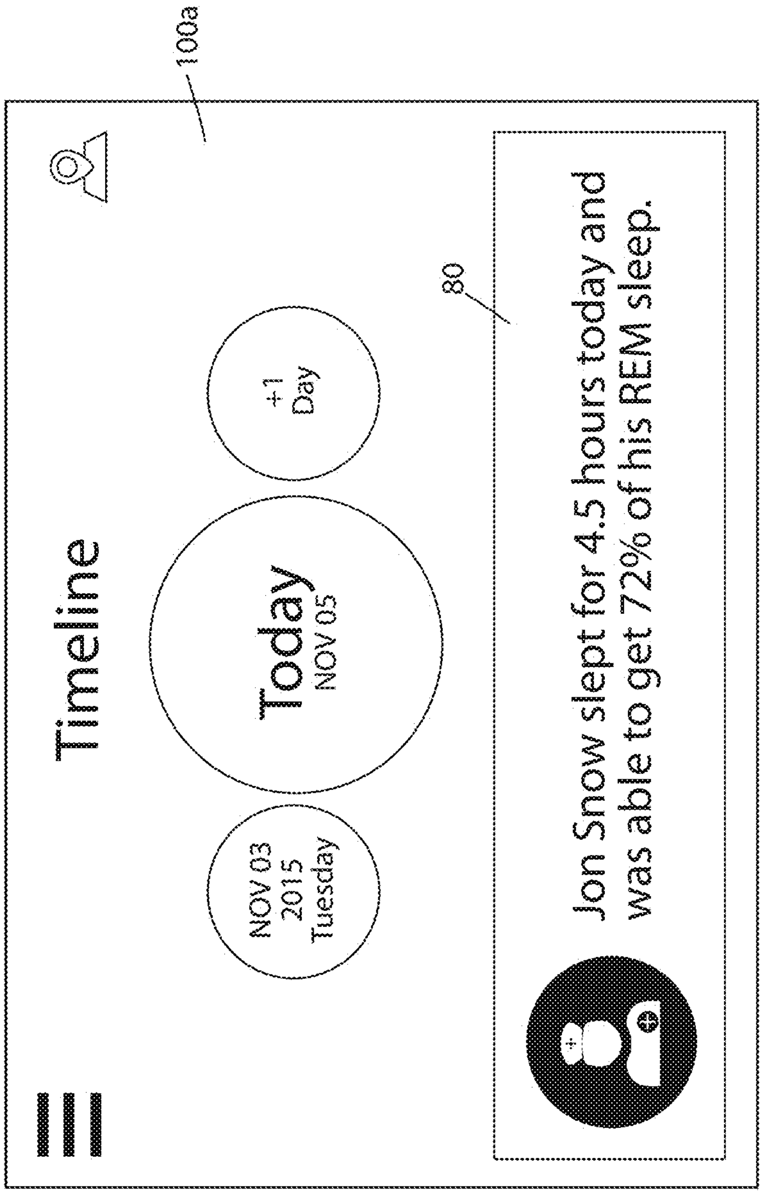
FIG. 10 is an another illustrative example of a screen shot displayable on the mobile electronic device showing detail about a specific event regarding the patient's hospital event.
Figure 11:
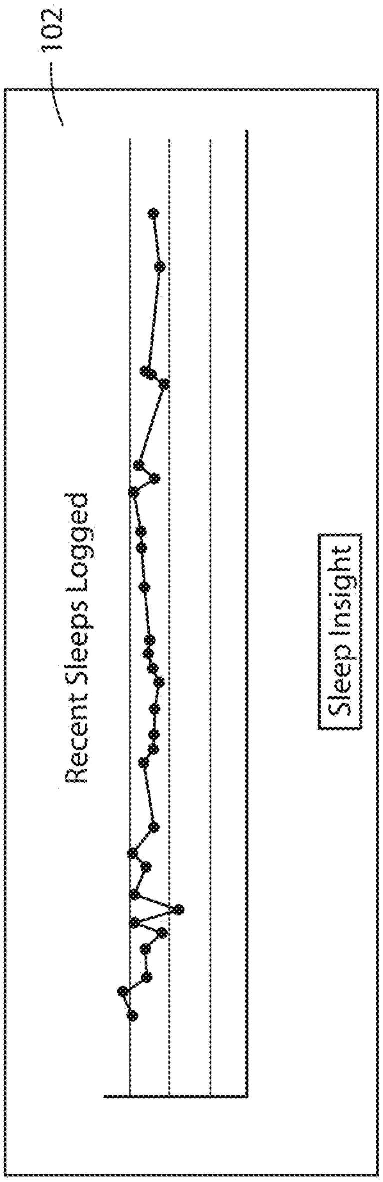
FIG. 11 is an illustrative example of a screen shot displayable on the mobile electronic device showing more detailed information regarding the event shown in FIG. 10.

As one example, FIG. 10 illustrates an alternative day listing screen 100*a*. The particular event 80 shown on day listing screen 100*a* is a report regarding the sleep quality of a particular patient. If a user selects this event 80, health info app 30 brings up a detailed screen 102, such as shown in FIG. 11, that shows more detailed information regarding the event. In this particular example, detailed screen 102 identifies additional details regarding quality of a patient's sleep. In one embodiment, this sleep information is retrieved from local vendor server 48 which receives this information from one or more sensors positioned on, or within, the patient's hospital bed. For example, in some embodiments of health information system 20, one or more beds or stretchers of hospital 22 have sleep sensors incorporated therein in the manner disclosed in commonly assigned U.S. patent publication 2016/0022218 filed Mar. 13, 2014, by inventors Michael Hayes et al. and entitled PATIENT SUPPORT APPARATUS WITH PATIENT INFORMATION SENSORS, the complete disclosure of which is hereby incorporated herein by reference. When equipped with such sleep sensors, the sleep sensors either communicate their data directly to local vendor server 48, or they communicate their sleep data to a different server on network 50 that then shares the sleep quality data with local vendor server 48. Local vendor server 48, in turn, shares the sleep quality data with the health info apps 30 that are operating within hospital 22 and that are permitted to receive such information.

As shown in FIG. 11, still more information regarding the patient's sleep may be available by selecting an additional information icon 104. When selecting additional information icon 104, further information regarding the patient's sleep, including detailed sleep quality information for individual days of the patient's visit may be displayed. Such additional information may include the amount of sleep the patient received each day, the quality of that sleep, the categorization of the sleep (amount of REM sleep, etc.), and/or the start and stop times of the sleep, including interruptions.

Figure 12:
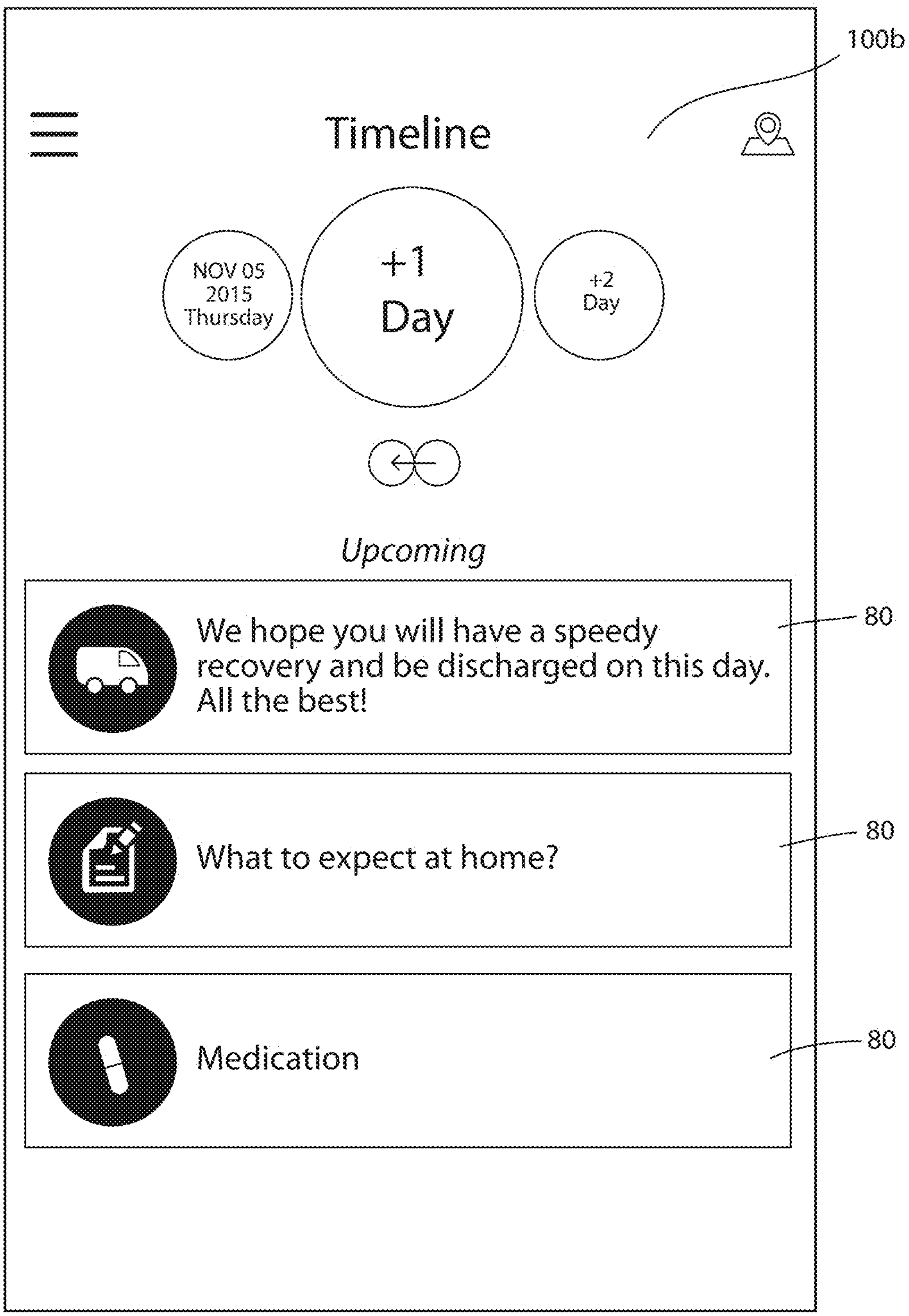
FIG. 12 is an illustrative example of a screen shot displayable on the mobile electronic device showing information regarding the patient's upcoming discharge from the hospital.
Figure 13:
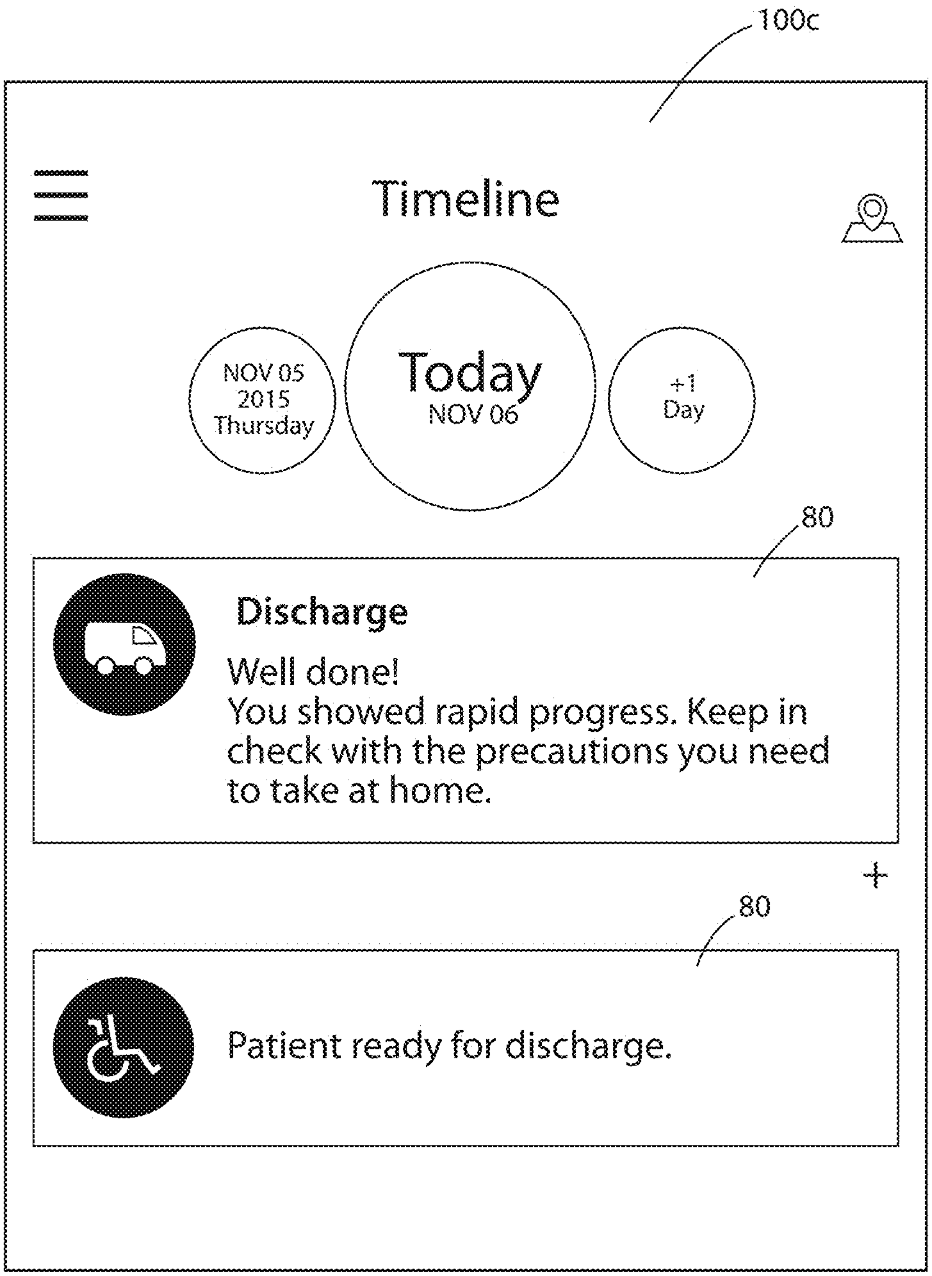
FIG. 13 is an illustrative example of a screen shot displayable on the mobile electronic device showing information regarding the patient's discharge.
Figure 14:
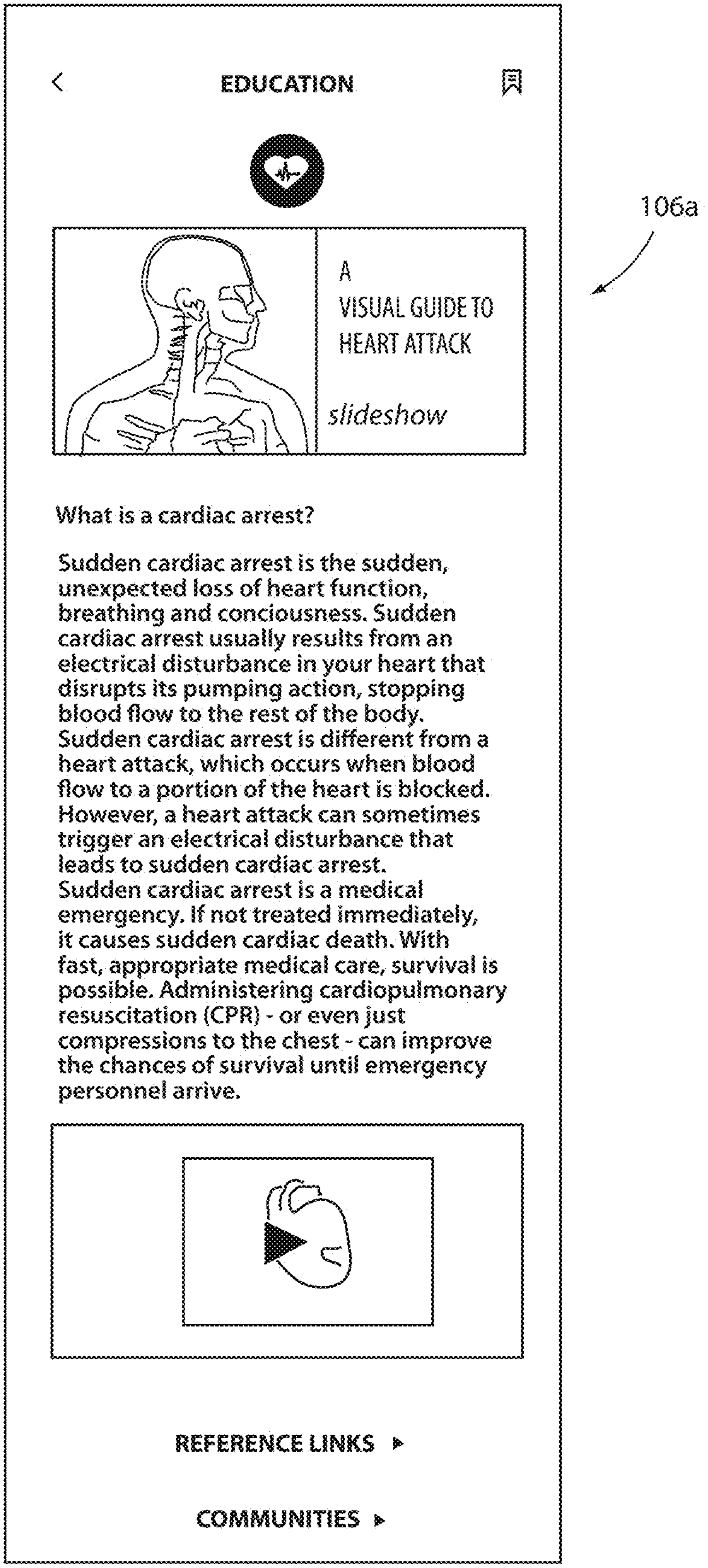
FIG. 14 is an illustrative example of a screen shot displayable on the mobile electronic device showing medical reference information related to the patient's condition and/or treatment.

FIGS. 12 and 13 illustrate still other day listing screens 100*b* and 100*c* that are displayable by health info app 30. Day listing 100*b* shows an illustrative listing of events that may occur for a patient prior to the patient being discharged from the hospital. Day listing 100*c* shows an illustrative listing of events that may occur on the day that a patient is discharged. As with the other day listings 100, a user may select any of the events 80 listed therein for further information.

Health info app 30 is configured to allow a patient, or the patient's spouse, to authorize the sharing of one or more types of information with friends and/or family members 34*h* and/or 34*i*. That is, a patient 34*d* and/or his or her spouse 34*e* are able to use health info app 30 to select what information they are willing to share about the patient's visit to hospital 22 with friends and family members 34*h* and 34*i*. The selection of what information to share and what information not to share is forwarded to local vendor server 48 which stores that information. When local vendor server 48 receives information from one or more servers on network 50, or from Internet connection 38, it determines whether the receiving information is to be shared with other users 34 who are associated with a particular patient (e.g. friends or family members of that patient). Information that is to be shared is forwarded to the devices 32 of the authorized recipients via Internet connection 38. Information that is not to be shared is forwarded, as appropriate, to only the device(s) 32 associated with the patient 34*d* and/or his or her spouse 34*e*.

In some embodiments, health info app 30 is configured to communicate with a bed server (not shown) that receives status information from the hospital beds. Such a bed server determines information about the patient, such as his or her sleep status (including, but not limited to, the amount of sleep, when the patient has fallen asleep or is awake, the quality of the sleep, the type of sleep, etc.), when he or she is present in the bed or absent from the bed, and other data regarding the patient's movement or activities while in the bed. This bed status information is forwarded to local vendor server 48 which, as appropriate, forwards it to one or more users 34.

For example, if a patient falls asleep and this is detected by sensors integrated into the patient's bed, the bed communicates a message to the bed server indicating that the patient has fallen asleep. This information is then forwarded by the bed server to local vendor server 48. Local vendor server 48 then updates a current status of the patient to being asleep. Any copies of health info app 30 that are installed on devices 32 that are authorized to receive information about that particular patient are then forwarded a message indicating that the patient is currently asleep. In some embodiments, the forwarded message is sent to those devices 32 immediately so that the devices can alert the users 34 of the change in the patient's status (i.e. having fallen asleep). In other embodiments, the health info app 30 does not receive the sleep status message until a user executes health info app 30 on his or her device 32. Health info app 30 and server 48 operate in a similar manner for other data received by server 48 that comes from other sources, such as EMR server 52 and/or other devices 32 (e.g. info entered from a caregiver 30's device who is associated with a particular patient). Still further, in some embodiments, the notification of an event detected by health info app 32 is forwarded to a patients' social media page, such as a Facebook page. The patient and other users of health info app 30 are able to configure which social media websites receive information from health info app 30.

Beds that are configured to detect when a patient has fallen asleep or is awake, when the patient is out of bed or has returned, the quality of the patient's sleep, and other characteristics regarding the patient's movement and activities are disclosed in commonly assigned U.S. patent publication 2016/0022218 filed Mar. 13, 2014, by inventors Michael Hayes et al. and entitled PATIENT SUPPORT APPARATUS WITH PATIENT INFORMATION SENSORS, the complete disclosure of which has already been incorporated herein by reference.

As noted previously, FIGS. 14 and 15 illustrate educational screens that are displayable in response to a user selecting education option 86 from main menu screen 82 (FIG. 6). Educational screen 106*a* provides more information to a user 34 of health info app regarding cardiac arrest. Educational screens, such as 106*a*, are provided by health info app 30 accessing data from one or more databases, including, but not limited to, database 58. In some embodiments, health info app 30 accesses educational information from one or more locations using the Internet access provided to local vendor server 48. Education screens 106 may also provide videos and/or other multimedia presentations that are viewable by a user of device 32. In some embodiments, such education content is streamed to the device 32 via streaming media server 54.

Educational screen 106*b* of FIG. 15 displays a plurality of conversations from an electronic chat room. Health info app 30 enables a user of a device 32 to read, participate in, and start conversations within a chat room that is maintained by hospital 22, a plurality of hospitals 22, another healthcare provider, and/or any entity interested in providing health-related chat rooms. In this manner, patients, as well as their friends and family, may engage in electronic conversations with other patients, and/or friends and families or other patients, regarding healthcare information. In this manner, a patient undergoing a particular medical treatment may be able to contact other patients who have undergone the same medical procedure. Further, questions of a patient may be answerable by other people who have participated in, or are participating in, the chat room.

Figure 16:
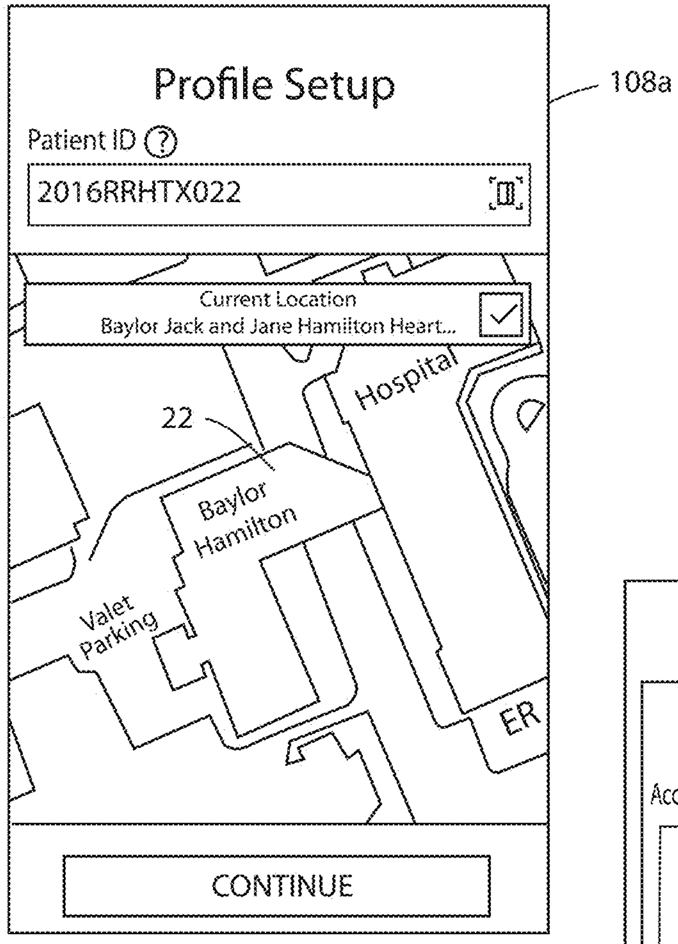
FIG. 16 is an illustrative example of a screen shot displayable on the mobile electronic device showing the hospital's location and parking information on a map.

FIGS. 16-19 illustrate navigation screens 108 that are displayable by health info app 30 in response to a user selecting wayfinding option 88 from main menu screen 82 (FIG. 6). Navigation screen 108*a* of FIG. 16 provides a map showing the location of hospital 22 with respect to its surroundings. Health info app 30 allows the user 34 to zoom in or out of the map of navigation screen 108*a*. In some embodiments, health info app 30 utilizes commercially available mapping services for displaying the information on screen 108*a*, such as, but not limited to, Google Maps.

Figure 17:
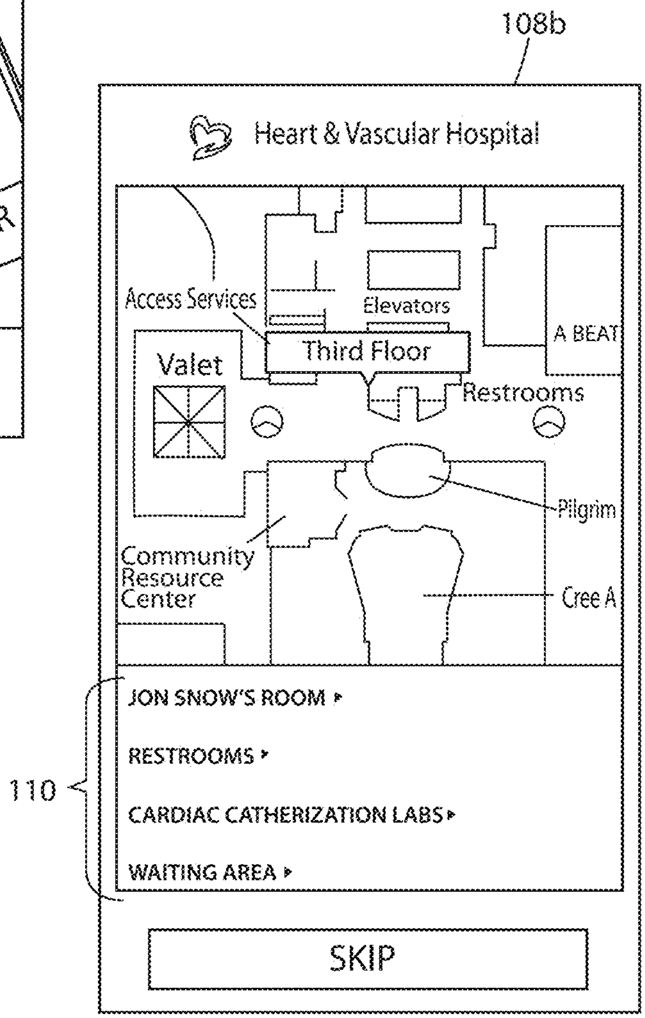
FIG. 17 is an illustrative example of a screen shot displayable on the mobile electronic device showing a floorplan of the hospital as well as a menu of items whose location may be of interest.
Figure 18:
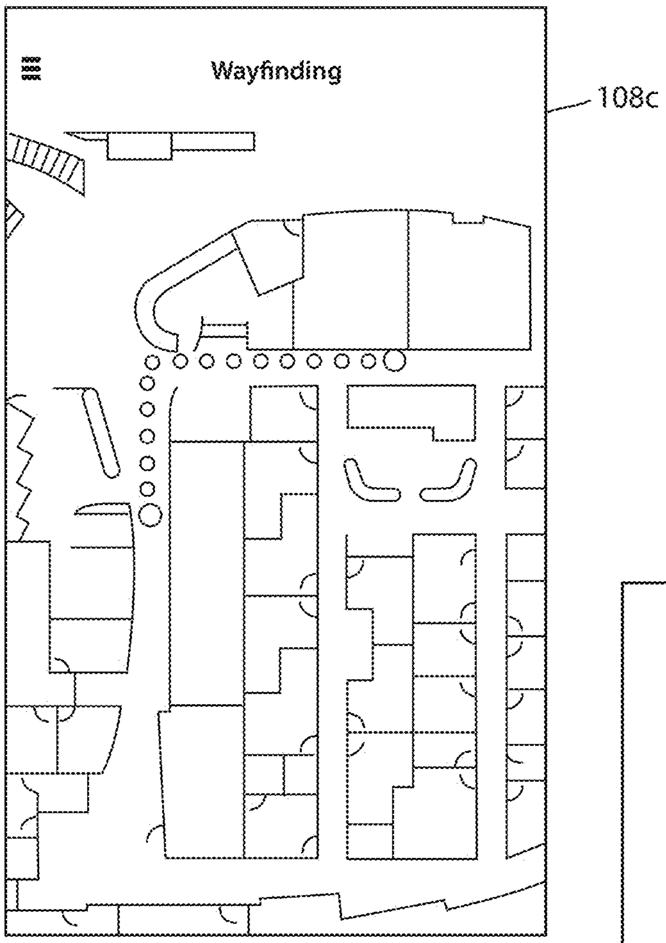
FIG. 18 is an illustrative example of a screen shot displayable on the mobile electronic device showing a more detailed layout of a floorplan of the hospital.
Figure 19:
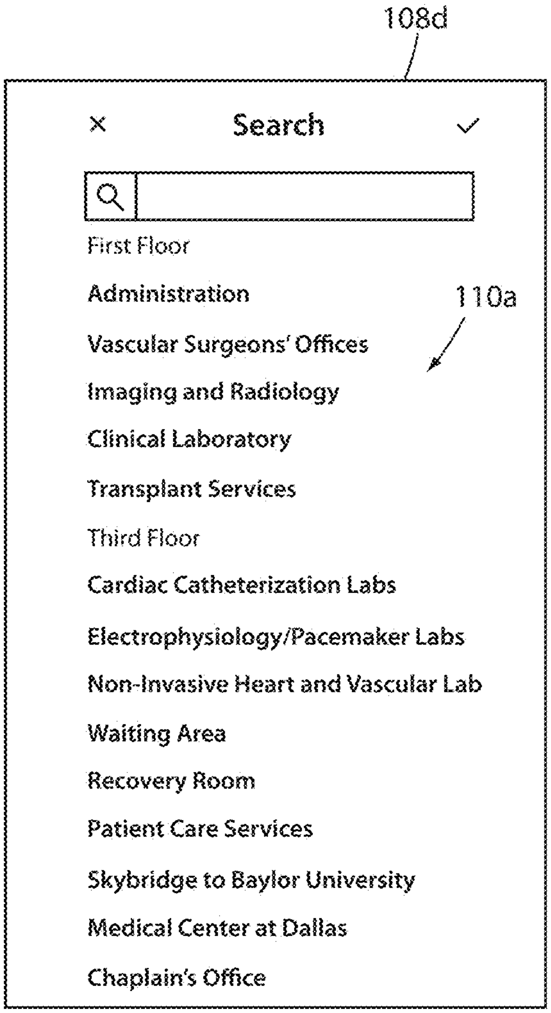
FIG. 19 is an illustrative example of a screen shot displayable on the mobile electronic device showing a more detailed menu of items whose location may be of interest.

Navigation screen 108*b* of FIG. 17 illustrates a more detailed map that includes portions of internal floor plans of hospital 22. Navigation screen 108*b* also includes a menu of locations 110. In response to selecting an item within menu 110, health info app 30 identifies the location of the selected menu item on a map and/or identifies the user's current location relative to the location of the selected item. Navigation screen 108*c* of FIG. 18 illustrates in even more detail a floor plan of the hospital 22 that identifies individual rooms within hospital 22. Navigation screen 108*d* illustrates a more detailed menu of locations 110*a* that a user may select. When selecting one of the items of menu 110*a*, health info app 30 displays the location of the selected item on a map and/or provides directions to the user of how to get to that location from his or her current location.

FIG. 20 illustrates an example of a patient information screen 112 that is displayable by health info app 30 in response to a user selecting patient info option 90 from main menu screen 82 (FIG. 6). Patient info screen 112 is only accessible to authorized users of health info app 30, such as authorized family members or friends of a particular patient 34*d*. Patient info screen 112 allows these authorized individuals to add information regarding the patient that may not have been added to the hospital's records. Thus, in the example illustrated in FIG. 20, a particular patient may have been admitted to the hospital 22 without the hospital entering the patient's race, ethnicity, preferred language, current medications, and/or allergies into its records. This information can be added by an authorized friend or family member by entering the missing information on patient information screen 112. This is accomplished by the friends or family members by using their copy of health info app 30 that is installed on their devices 32. Those devices 32 then communicate this information to local vendor server 48.

Local vendor server 48 forwards the information entered on patient information screen 112 to EMR server 52 and/or to any other server located within hospital 22 that the hospital administration has designated. The information is then available to the hospital personnel. In some embodiments, the information is flagged as having been entered by a friend or family member, rather than a hospital employee, so that viewers of the information are apprised of the source of the information. In addition, some embodiments of health info app 30 allow friends or family members to change information that was previously entered by hospital personnel, but which may be mistaken. In these embodiments, health info app 30 maintains both the incorrectly entered information and the family-supplied corrected information so that viewers can see both data entries. Appropriate individuals at the hospital 22 may then be tasked with rectifying such data discrepancies.

Figure 21:
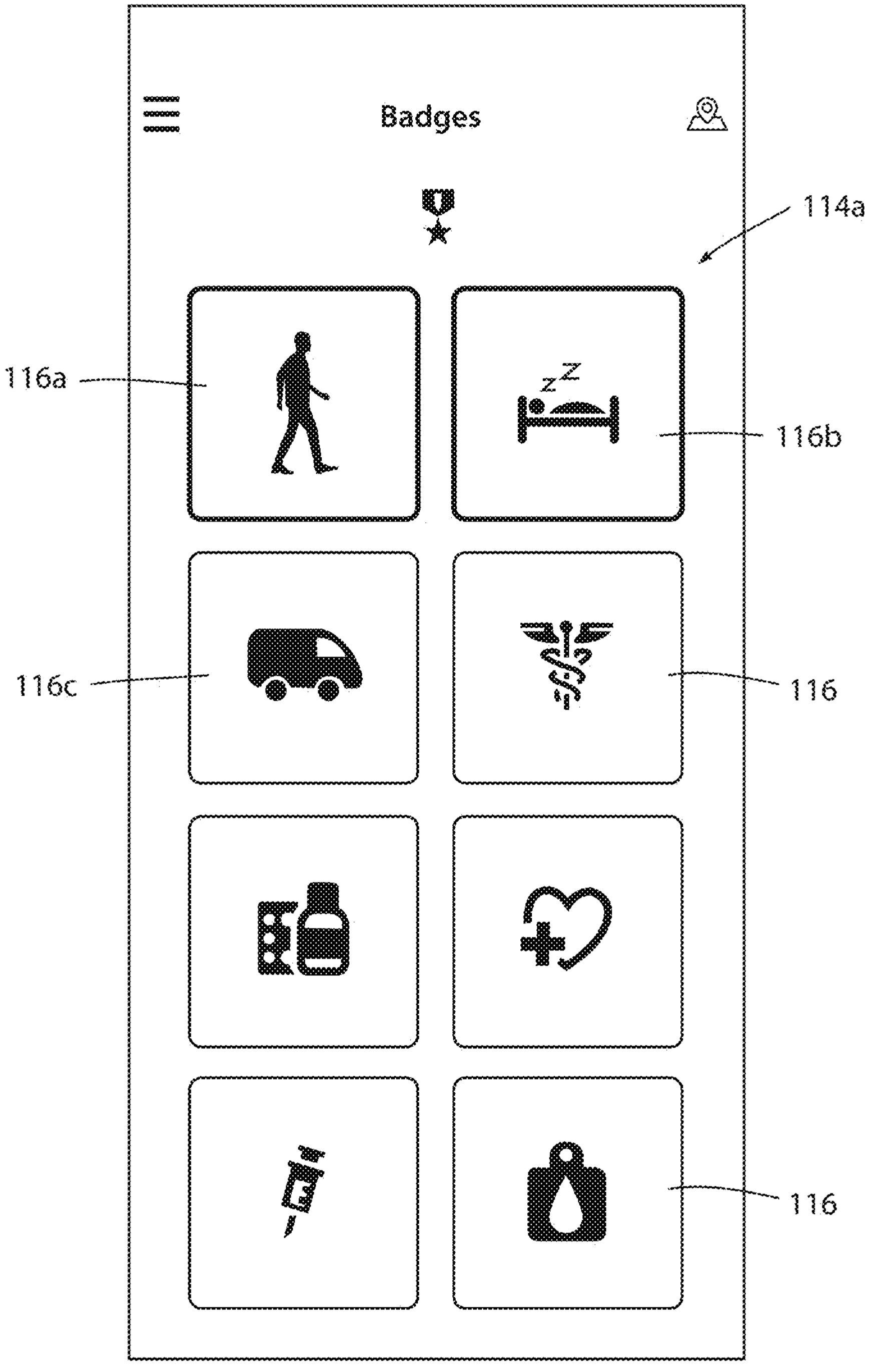
FIG. 21 is an illustrative example of a screen shot displayable on the mobile electronic device showing a plurality of badges that the patient may be able to earn while at the hospital.
Figure 22:
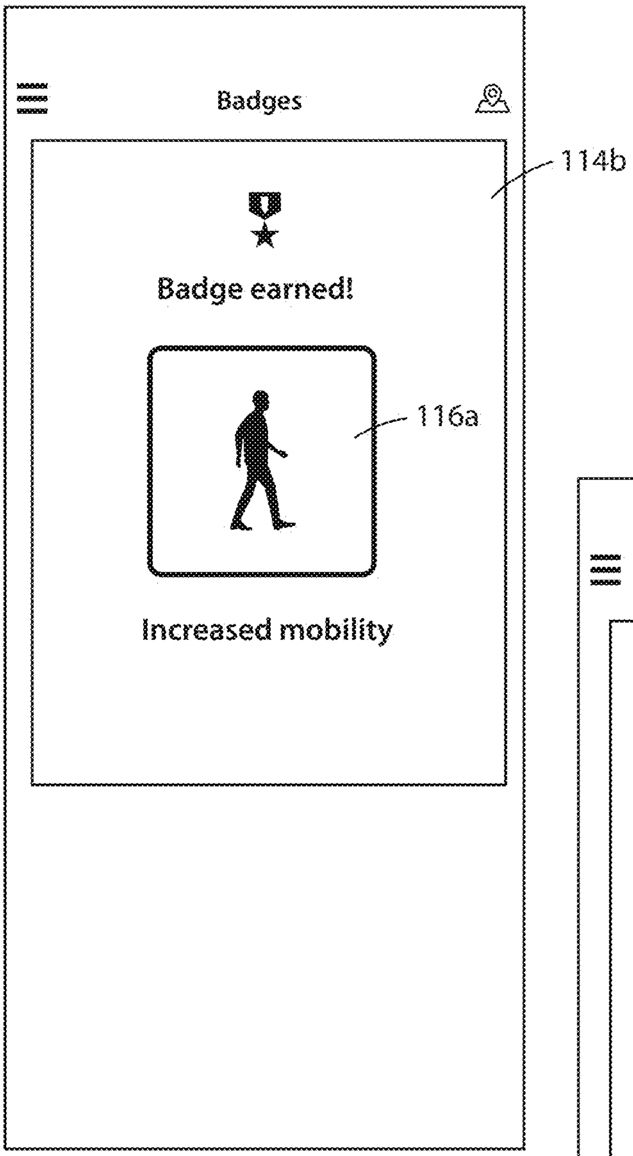
FIG. 22 is an illustrative example of a screen shot displayable on the mobile electronic device showing a notification message that the patient has earned a mobility badge.

FIG. 21-24 illustrate examples of badge screens 114 that are displayable by health info app 30 in response to a user selecting badge option 92 from main menu screen 82 (FIG. 6). Badge screens 114 are displayed to show a patient's progress in achieving one or more badges, or other types of milestones, while they are at hospital 22. Badge screen 114*a* of FIG. 21 illustrates a plurality of badges 116 that are achievable by a particular patient at a particular hospital 22 (and which may vary depending upon the reason for the patient's visit to the hospital). In the example shown in badge screen 114*a*, two of the badges 116*a* and 116*b* are highlighted in a different color in order to show that those two badges have been achieved by that particular patient.

Badge 116*a* is awarded to a patient when the patient has achieved a mobility milestone. The mobility milestone may vary from patient to patient and condition to condition, but is generally an achievement that is awarded when the patient has reached a predetermined level of mobility. This may include the patient sitting up on his or her own, entering or exiting his or her bed without assistance, being out of bed for a predetermined amount of time, or still other types of mobility thresholds. In some embodiments, the mobility of the patient is measured by one or more sensors that are integrated into the patient's bed and which report their data to local vendor server 48. The information from such sensors may be augmented by one or more additional sensors that track the amount of movement of the patient when he or she is out of bed.

In some embodiments, the beds at hospital 22 include mobility sensors such as those disclosed in commonly assigned U.S. patent publication 2016/0106345 filed by inventors Marko Kostic et al. and entitled PERSON SUPPORT APPARATUSES WITH MOTION MONITORING, the complete disclosure of which is incorporated herein by reference. Still further, in some embodiments, one or more mobility sensors of the type disclosed in commonly assigned U.S. patent application Ser. No. 14/928,513 are used for tracking the movement of a patient while in bed and/or out of bed. U.S. patent application Ser. No. 14/928,513 is commonly assigned to the assignee of the present application and was filed Oct. 30, 2015, by inventors Richard Derenne et al and entitled PATIENT SUPPORT APPARATUSES WITH PATIENT MOBILITY MONITORING, the complete disclosure of which is hereby incorporated herein by reference. Health info app 30 may also derive mobility information from EMR 52 and/or other sources.

Figure 23:
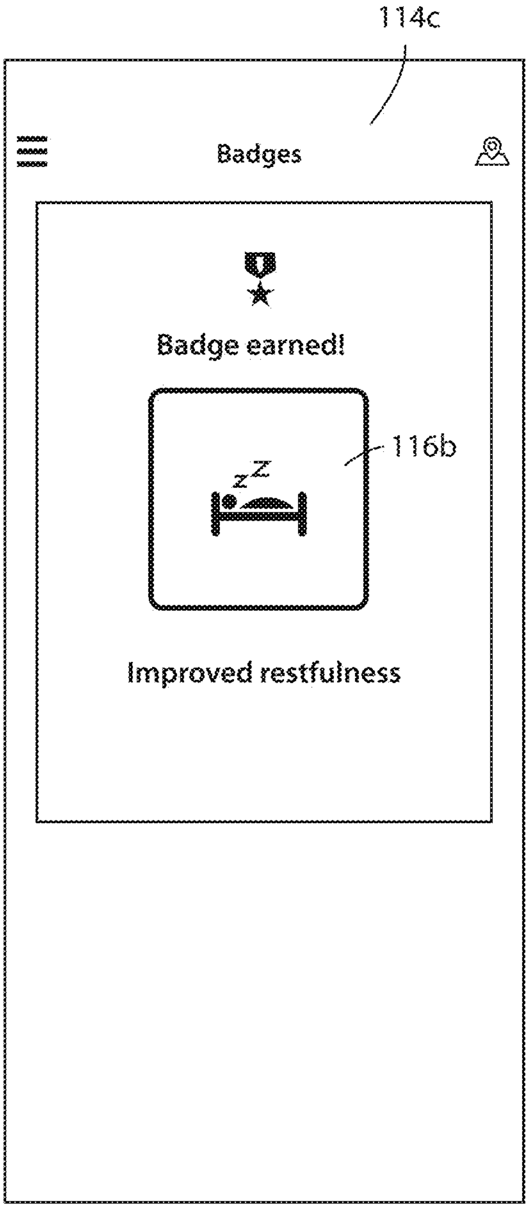
FIG. 23 is an illustrative example of a screen shot displayable on the mobile electronic device showing a notification message that the patient has earned an improved restfulness badge.

Badge 116*b* of FIG. 23 may be awarded when a patient has achieved one or more sleep milestones while in hospital 22. The determination of these sleep milestone may be carried out in any of the manners described above with respect to FIG. 11. Sleep milestones may also be determined by consulting data stored in EMR 52. Regardless of where the data is stored and the source of such data, health info app 30 awards badge 116*b* when one or more milestones relating to sleep are achieved. Administrators and/or healthcare professionals at hospital 22 are able to use their copies of health info app 30, along with their administrator status for health info app 30, to input and change the sleep milestone for which a patient is to be rewarded with a badge. That is, hospital 22 is able to custom tailor the sleep badges 116*b* according to whatever thresholds it desires, including customizing the thresholds to individual patients. Similar customization and threshold selections are available to authorized individuals of the hospital 22 for all of the other badges 116 discussed herein.

Figure 24:
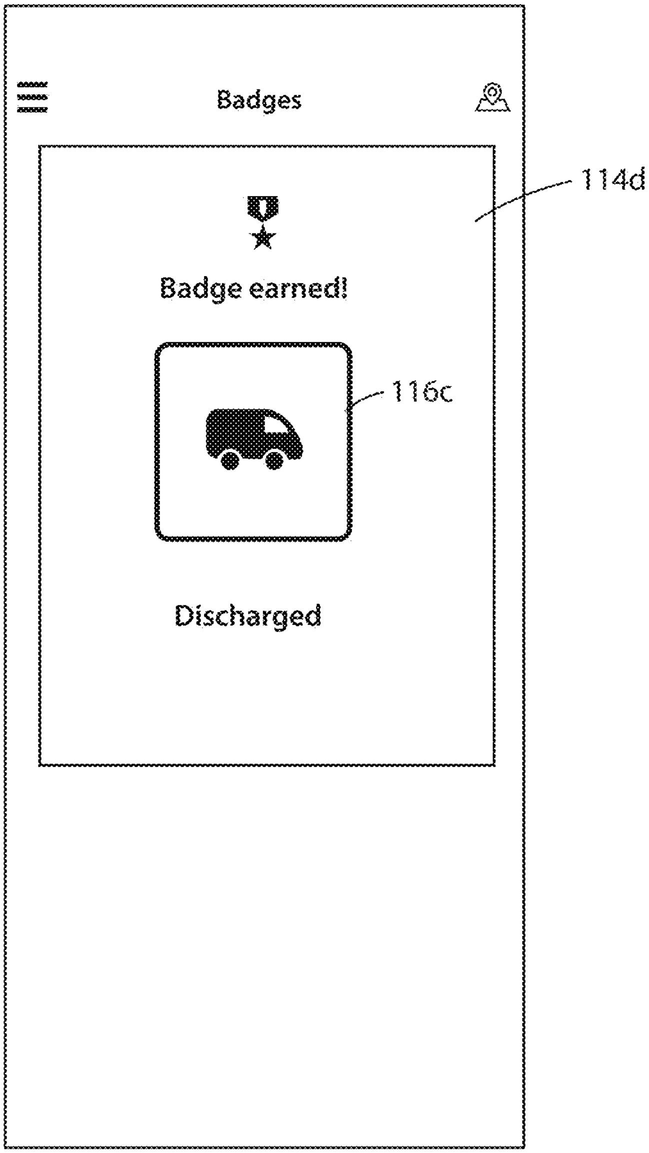
FIG. 24 is an illustrative example of a screen shot displayable on the mobile electronic device showing a notification message that the patient has earned a discharge badge.
Figure 25:
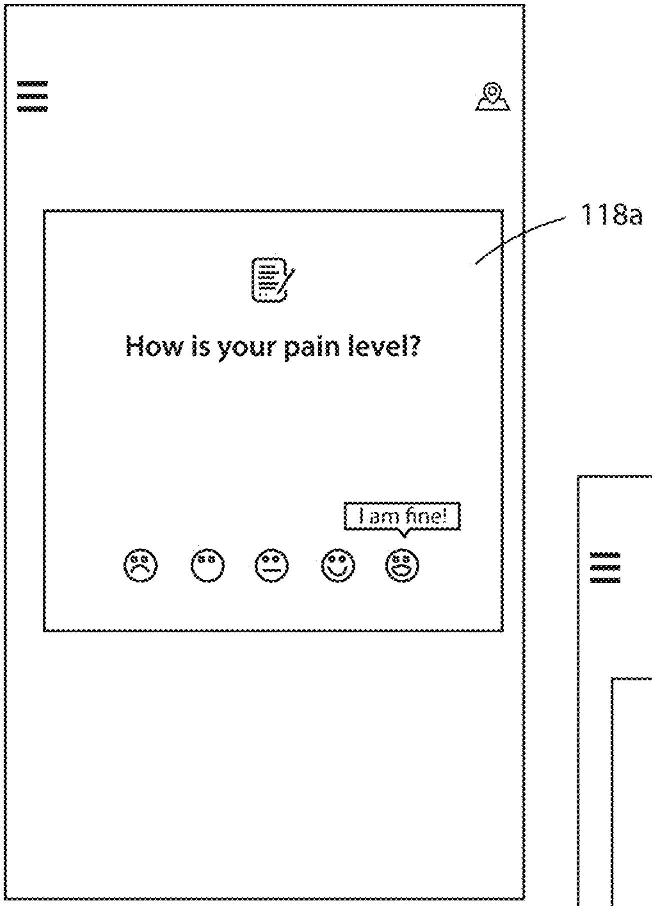
FIG. 25 is an illustrative example of a screen shot displayable on the mobile electronic device showing a patient question regarding his or her pain level.

FIG. 24 illustrates a discharge badge 116*c* that is awarded to a patient when he or she has recuperated sufficiently to be able to be discharged from hospital 22. Other badges 116 may also be illustrated, including, but not limited to, badges relating to eating, medications, treatments, procedures, etc. In some embodiments, health info app 30 is configured to allow caregivers to add comments to the badges. Such comments are added through the use of the caregiver's health info app 30, which is configured to allow them to enter comments for specific patients under their care. Health info app 30 is also configured to allow authorized hospital administrators to design their own badges and the criteria for awarding them, thereby allowing hospitals 22 to tailor their badges in any manners they see fit.

FIGS. 25-28 illustrate examples of feedback screens 118 that are displayable by health info app 30 in response to a user selecting feedback option 94 from main menu screen 82 (FIG. 6). Feedback screens 118 allow a patient (and in some cases people other than the patient, such as the patient's spouse 34*e* and/or family members 34*i*) to provide feedback to the hospital about different aspects of the patient's stay at the hospital. For example, feedback screen 118*a* of FIG. 25 asks a patient to rate his or her pain level. In the illustrated example, this question is answered based upon a five option rating system. Other rating systems for assessing a pain level can, of course, be used. Regardless of the specific rating scale, the patient's answer is relayed by health info app 30 to the appropriate personnel within hospital 22, such as, but not limited to, the caregivers assigned to that particular patient. This feedback may be forwarded to those caregivers via mobile information server 60, which may send the patient's answers directly to the smart phone 32*a*, badge, pager, or other mobile device that is associated with the patient's caregivers. In this manner, the caregivers are provided with up-to-date feedback from the patient, even if they are not in the room with the patient. Timely intervention can then be undertaken.

Figure 26:
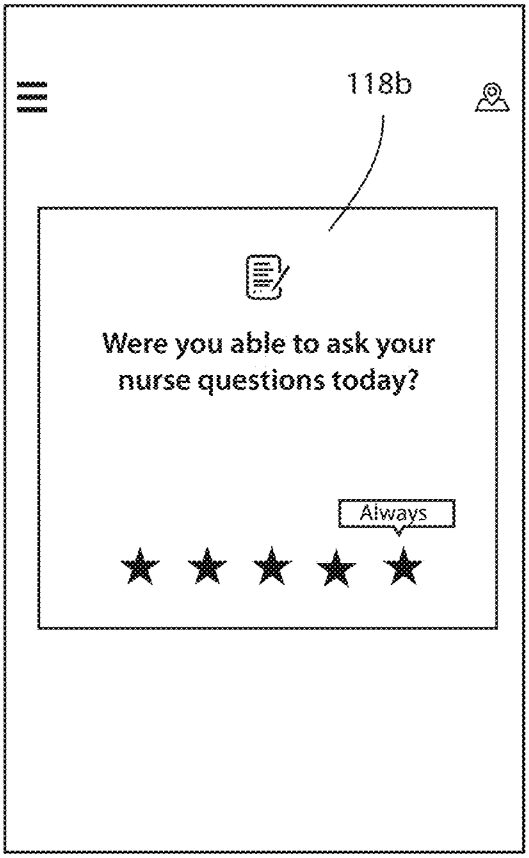
FIG. 26 is an illustrative example of a screen shot displayable on the mobile electronic device showing a patient question regarding his or her nurse.
Figure 27:
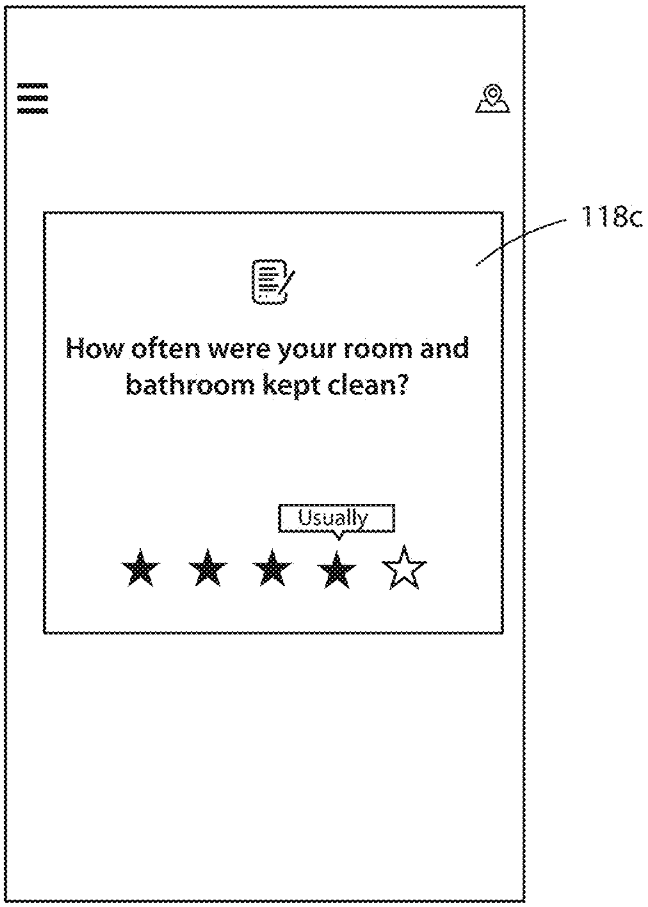
FIG. 27 is an illustrative example of a screen shot displayable on the mobile electronic device showing a patient question regarding his or her restroom.

FIG. 26 shows another example of a feedback screen 118*b* that may be displayed to inquire about the quality of nurse communications. Depending upon how a particular hospital 22 configures health info app, the patient's answer to the question of FIG. 26 may be forwarded to an administrator or manager instead of to the patient's caregiver. Such administrators are then informed of the patient's assessment of caregiver communications and can take responsive action, as deemed appropriate.

Feedback screen 118*c* illustrates an inquiry to the patient regarding the cleanliness of his or her restroom. As with the other feedback screens 118, the patient's response to this screen may be forwarded to individuals that are custom selected by the hospital. That is, instead of forwarding the patient's answer to the inquiry of FIG. 27 to a caregiver, this response may be forwarded to appropriate personnel in the hospital's janitorial or cleaning department.

The types of feedback screens 118*a-c* shown in FIGS. 24-27, as well as other feedback inquiries, are displayed on the user's screen not only in response to the user selecting feedback option 94 of main menu 82 (FIG. 6), but also in response to the passage of time and/or the occurrence of certain events. Thus, for example, a feedback screen 118 is presented in some embodiments automatically every morning that requests patient feedback regarding how well the patient slept. Another feedback screen 118 may be automatically generated after every meal requesting feedback about the quality of the patient's meal. Yet another feedback screen may automatically be generated after a caregiver exits the patient's room that inquires how well the caregiver explained information (the caregiver's exit may be determined by a conventional tracking system installed in hospital 22 that communicates with a tracking server on network 50 that is in communication with local vendor server 48). Still other feedback inquiries may be configured to automatically appear on the screen of the user's device 32 based upon the time of day and/or one or more events associated with the patient. Depending upon the specific inquiry, the patient's answers are forwarded to the appropriate personnel within hospital 22 using mobile information server 60 and/or other servers on network 50.

Figure 28:
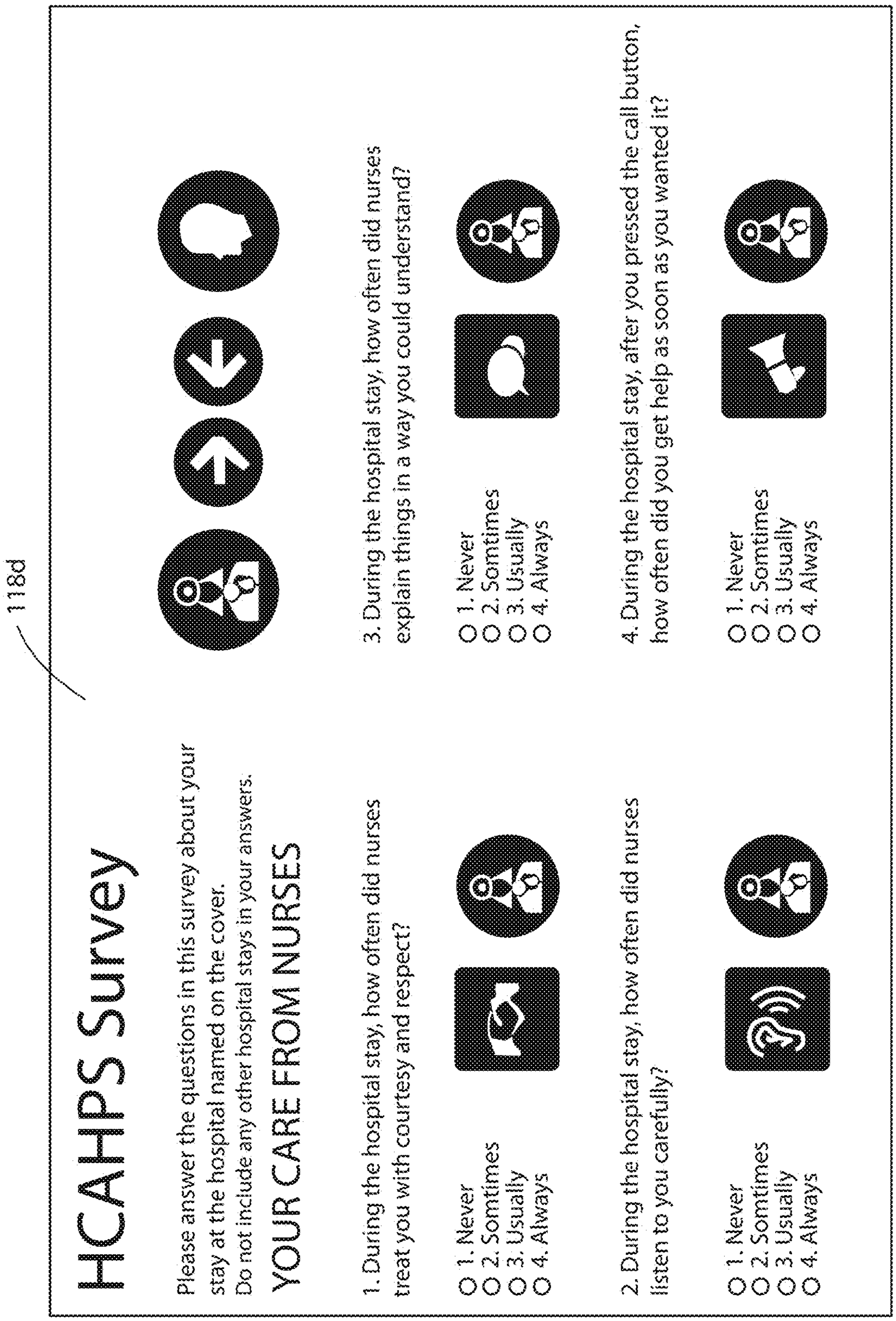
FIG. 28 is an illustrative example of a screen shot displayable on the mobile electronic device showing patient questions used as part of an HCAHPS survey.

FIG. 28 illustrates a feedback screen 118*d* that illustrates a portion of an HCAHPS survey. The acronym HCAHPS refers to Hospital Consumer Assessment of Healthcare Providers and Systems. HCAHPS surveys are a set of questions that are asked of patients regarding their visit to a particular hospital. The results of such surveys are forwarded to administrators of hospital 22. Hospital 22 also forwards the results of these surveys to a central repository in accordance with federal law. Compilations of the results are then made available to the public.

In some embodiments, health info app 30 is configured to automatically present a feedback screen, such as screen 118*d* of FIG. 28, to the user at or about the time the patient is being discharged from hospital 22. In this manner, the patient is more likely to take the time to fill in responses to the survey (as opposed to mailing the survey to the patient's home and asking him or her to fill out the survey after they've left the hospital). The automatic presentment of this HCAHPS screen 118*d* may be accompanied with an aural or vibratory notification on the patient's electronic device 32 (such as smart phone 32*a*) so that the patient 34*d* is alerted to the fact that health info app 30 is requesting the attention of the patient. Similar aural or vibratory notifications may be generated at other times when health info app 30 has information to display that is of importance.

Figure 29:
FIG. 29 is an illustrative example of a screen shot displayable on the mobile electronic device showing a text or chat feature for enabling patient-caregiver communications.
Figure 30:
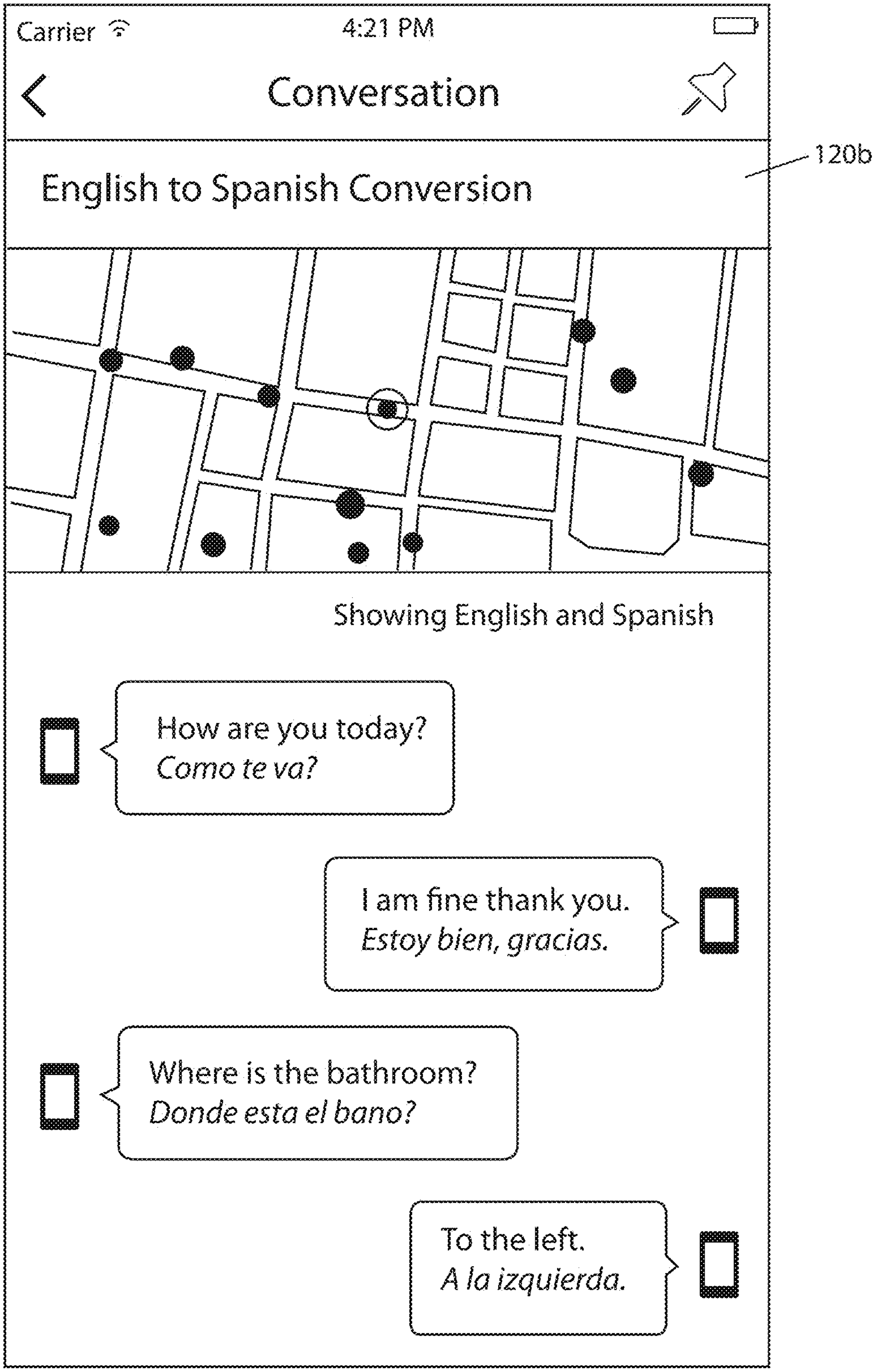
FIG. 30 is an illustrative example of a screen shot displayable on the mobile electronic device showing a language translation feature for facilitating cross language communication.

FIGS. 29-30 illustrate examples of communication screens 120 that are displayable by health info app 30 in response to a user navigating to these screens. Although FIG. 6 does not illustrate a communication option on the main menu screen 82 displayed therein, this main menu screen 82 may be modified to include a communications option that, when selected, brings up one or more communication screens 120 such as shown in FIGS. 29-30. Communication screens 120 may also be accessed by a user 34 of health info app 30 in other manners. Regardless of how accessed, communication screen 120*a* of FIG. 29 displays a chat feature of health info app 30 that allows a patient 34*d* to communicate with his or her caregivers, such as nurse 34*c*. This communication takes place via health info app 30 communicating messages to local vendor server 48 which forwards those messages to mobile information server 60. Mobile information server 60, in turn, forwards the messages to the device 32 associated with the nurse 34*c* to whom the patient is communicating. Messages from the nurse 34*c* are sent back to the patient's device 32 in the same manner.

Communication screen 120*b* of FIG. 30 illustrates a translation feature of health info app 30. This translation feature is, in some embodiments, both textual and aural. When textual, the translation feature translates text, such as that entered when chatting in the manner illustrated in FIG. 29, from one language to another language. This enables a patient who does not speak the language of the caregivers within a hospital 22 to communicate more easily with the caregivers. When the translation feature is aural, the patient, or other user 34, speaks into the electronic device 32 and the health info app 30 detects the speech from the microphone of the electronic device 32. Health info app 30 translates the detected speech into the desired language and generates speech in that language using the speaker(s) of the electronic device 32. Either of both of these translation features may utilize known translation software. Further, in some embodiments, health info app 30 forwards the input text and/or detected speech to another computer or service that is accessible to health info app 30 via local vendor server 48 (and its connection both network 50 and the Internet), and that other computer and/or service performs the translation and sends the translated result back to the device 32 from which the text or speech originated.

It will of course be understood that the information described above that is displayable to a user 34 of health info app 30 can vary from the specific information shown and discussed. Menu 82 may include different options from that illustrated, as well as more or fewer options. In some embodiments, health info app 30 also displays information for a patient prior to his or her scheduled visit that may be useful to the patient. This information may include such things as such as dietary restrictions, driving directions, check-in information, etc. Once the patient arrives at hospital 22 (as detected by the geolocation fencing feature described above), health info app 30 may display additional information to the patient, such as the wait times for clinical procedures, a question log for nurses, education material, bed controls, etc. After the patient leaves hospital 22, or is about to leave the facility, still other information is displayable by app 30, such as discharge procedures, post-visit dietary restrictions, medications, etc.

FIGS. 31-42 illustrate features and screens of health info app 30 that relate to management of one or more medical devices in hospital 22 and/or to one or more administrative tasks of hospital 22. As a result, the screens and features illustrated in these FIGS. are not intended to be used by patients **34*d* and/or the patient's friends or family. Instead, these features and screens are intended for use by hospital personnel and/or outside support technicians who communicate with the hospital staff. As a result, health info app 30 limits access of these screens and features to only authorized personnel. Indeed, in some embodiments, as mentioned previously, the content and features shown in these FIGS. are incorporated into a separate health info app that is independent of the health info app 30 described above. However, for purposes of the following written description, these features and content will be described as being part of health info app 30**, although it will be understood that they could be implemented as a separate application, or multiple separate applications.

Figure 31:
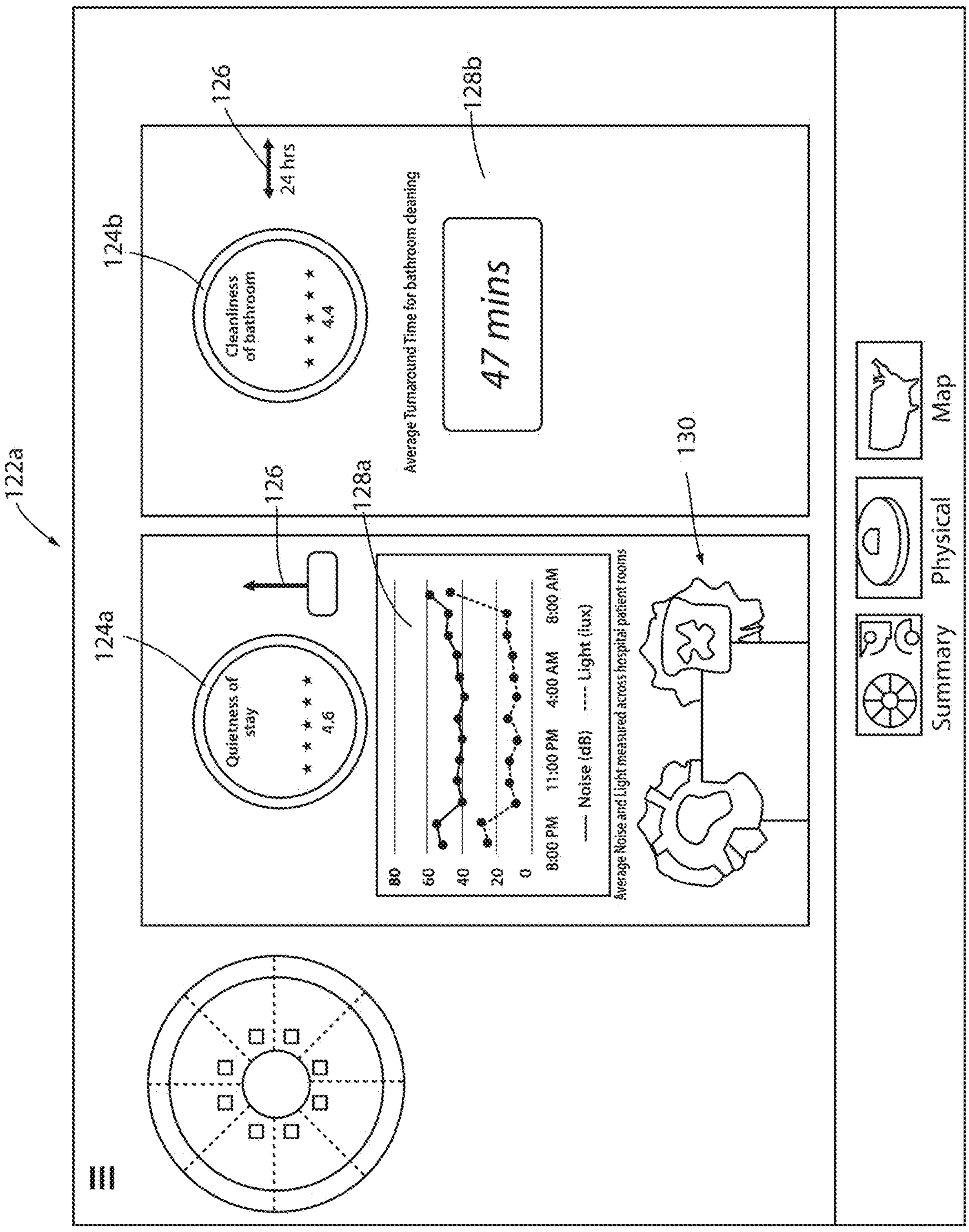
FIG. 31 is an illustrative example of a screen shot displayable on the mobile electronic device showing HCAHPS survey information.
Figure 32:
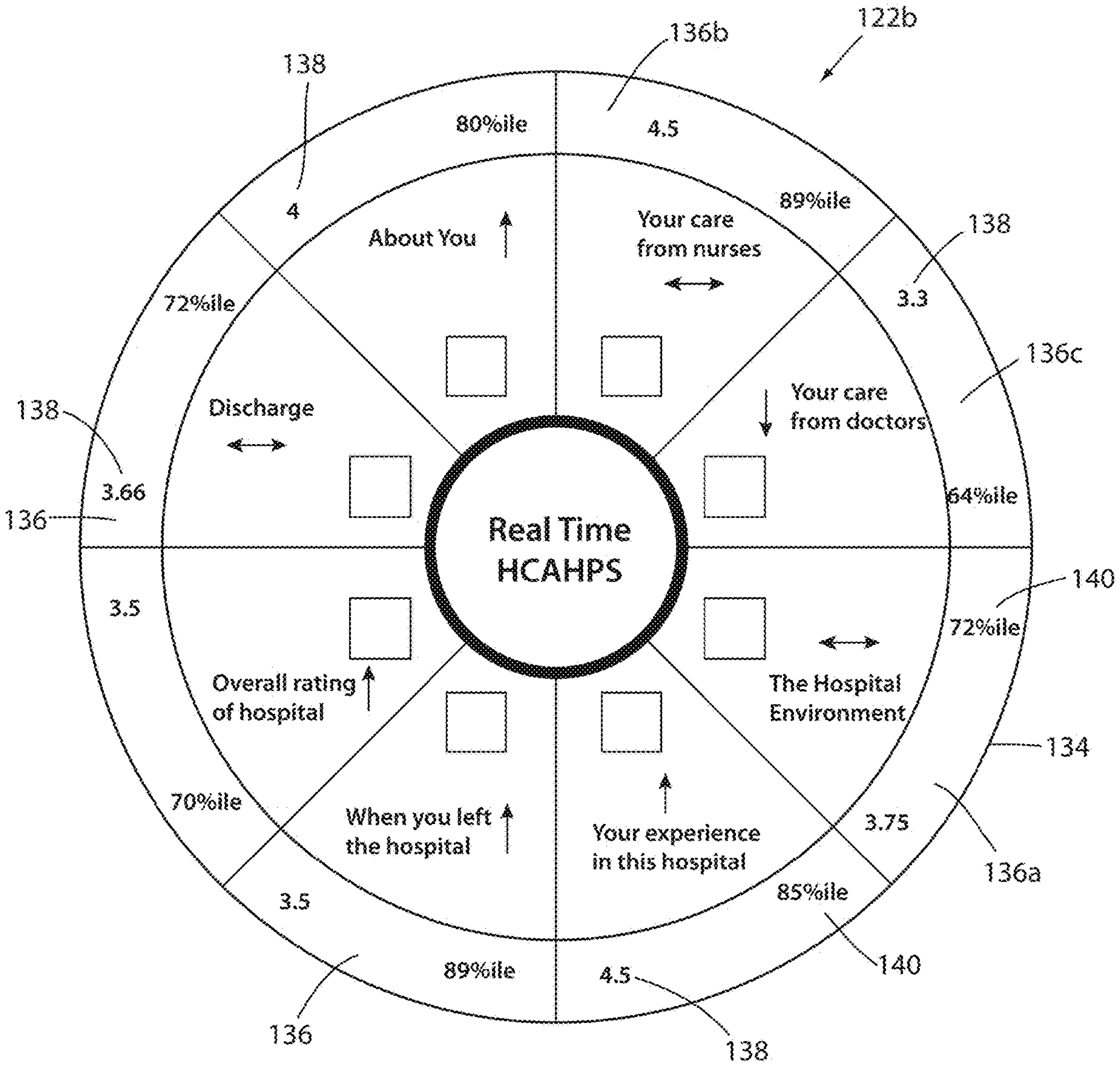
FIG. 32 is an illustrative example of a screen shot displayable on the mobile electronic device showing categories of HCAHPS survey information relative to historical data.

FIGS. 31 and 32 illustrate feedback summary screens 122 that gather, process, analyze, and display the results of the feedback provided by patients **34*d* using the feedback screens 118 discussed above. Feedback summary screen 122*a* of FIG. 31 includes a plurality of individual questions summaries 124 that summarize the results from a plurality of patients 34*d* to specific questions. For example, question summary 124*a* summarizes the results of patient responses to inquiries regarding the quietness of the patients' stays at hospital 22. This summary includes a presentation of the average of the responses received (4.6 in this case), as well as a trend indicator 126 indicating the trend (up, down, or constant) of responses over the last 24 hours. Summary 124*b* presents similar information for patient responses to the specific question of how clean the bathrooms were perceived to be by the patients 34*d***.

In addition to presenting individual question summaries 124, feedback summary screen **122*a* of FIG. 31 illustrates detailed summaries 128 regarding one or more of the feedback questions presented to patients 34*d*. Detailed summaries 128 provide additional information about specific inquiries that goes beyond what is shown in question summaries 124. For example, detailed summary 128*a* illustrates actual noise level measurements taken in patients' rooms over a given time period. These noise measurements are taken by microphones, or other sound sensors, positioned in the patient rooms of hospital 22 and, in some embodiments, other locations outside of the patient's rooms. The outputs from these sensors are fed to a server on network 50 that shares the results with local vendor server 48. Local vendor server 48, in turn, shares the results with those health info apps 30** that are authorized to receive this data.

In addition to including sound data, detailed summary **128*a* of FIG. 31 also displays actual light measurements that are taken in the patients' rooms over a given time period. These light measurements are taken by light sensors who communicate their measurements to a server on network 50. That server shares the results with local vendor server 48 which in turn forwards the results to those health info apps 30 that are authorized to receive this data. In some embodiments, health info app 30 is also configured to display a graphical map 130 showing measured noise and/or sound levels for one or more rooms over a given time period. The values of the measurements are displayed in a color coded fashion to indicate different measured intensities of the sound and/or light. Detailed summary 128** therefore provides measured values of sound and/or light along with the results of the patients' responses to inquiries about the quietness of their stay. This simultaneous presentation of subject and objective data allows hospital personnel to view and understand correlations between the patient's subjective observations and the objective measurements of the various sound and light sensors.

As shown in FIG. 31, detailed summary **128*b* shows the average time taken for the patient's restrooms to be cleaned. This information is provided to health info app 30 via communications with one or more of the servers on network 50 that receive data from the janitorial staff of hospital 22. The janitorial staff inputs information into the server, which is shared with local vendor server 48, after they are finished cleaning each restroom in hospital 22. Health info app 30 pulls this information from the janitorial server and displays it on feedback summary screens, such as screen 122*a* of FIG. 31**.

FIG. 31 also includes an HCAHPS score summary icon 132. When a user selects icon 132, health info app 30 brings up an HCAHPS summary 134, such as the one shown in FIG. 32. HCAHPS summary 134 is shown as a circle dividing into a plurality of sections 136. Each section 136 corresponds to a section of the HCAHPS survey. For example, section **136*a* relates to the hospital environment; section 136*b* relates to the care from nurses; section 136*c* relates to the care from doctors. Each section 136 includes an average score 138 indicating the average scores received by the hospital from its patient's for those questions on the HCAHPS survey that fall within the particular category of that section 136. Each section 136 also includes a percentile indicator 140 that indicates the percentile of the hospital's scores for the HCAHPS survey questions relating to the subject matter of the corresponding section 136. Thus, for example, HCAHPS summary 134 of FIG. 32 indicates that the hospital scored in the $72^{nd}$ percentile for the questions relating to the hospital environment (section 136*a***).

The percentile indicators 140 are based on a comparison of the hospital's scores to the national scores for those HCAHPS sections, in some embodiments. In some embodiments, health info app 30 is configured to allow health care administrators compare their HCAHPS scores to any other geographic area of interest. Such geographic areas include cities, counties, states, regions of the country, and the entire country. Health info app 30 is also configured to allow hospital administrators to compare their HCAHPS scores to other specific hospitals 22. The HCAHPS scores from other hospitals are pulled by health info app 30 from one or more existing Internet-accessible national databases that store the scores and make them available to hospitals.

Health info app 30 is configured to share patient answers to feedback questions, such as the HCAHPS survey, as well as other feedback question, with hospital personnel immediately. In this manner, appropriate hospital personnel can receive certain types of feedback from the patients while the patients are still in hospital 22. This gives the hospital the opportunity to address any issues the patient may be having prior to the patient leaving. This may improve the overall experience of the patient as well as lead to higher scores on the HCAHPS survey for the hospital.

In some embodiments, health info app 30 is adapted to present questions to the patients that are customized by the hospital administrators. The hospital administrators can therefore ask about specific items of interest to them. Further, health info app 30 is configurable by the hospital administrators in terms of the timing of those questions. Consequently, the hospital administrators can determine not only the content of one or more questions to the patients, but also the timing of those questions, the frequency of questions, and/or the overall amount of questions. Still further, the questions may be custom tailored based upon the reasons for the patient's stay at the hospital, based upon his or her caregivers, based upon the location of the patient in hospital 22, and/or based upon other factors. In this manner, specific questions may be presented to the patients that give the administrators more focused feedback on areas of potential interest to the administrators.

Figure 33:
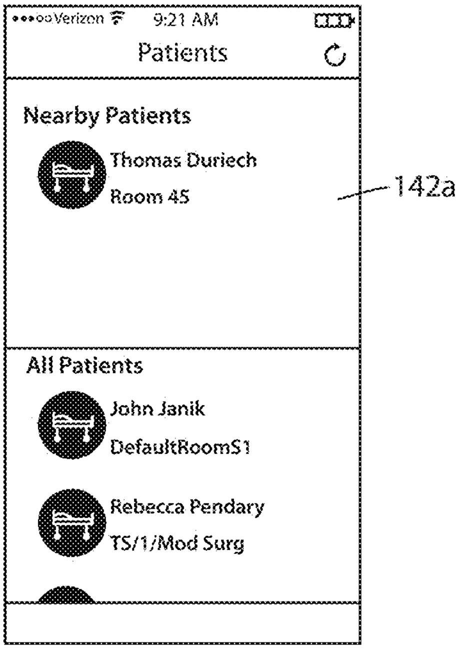
FIG. 33 is an illustrative example of a screen shot displayable on the mobile electronic device showing a list of patients and status information regarding the patients.

FIGS. 33-37 illustrate rounding screens 142 that are presented by health info app 30 to caregivers of hospital 22. Rounding screens 142 assist the caregivers in performing their rounding duties and documenting their work. Rounding screen 142*a* of FIG. 33 presents a list of patients. The list may be sorted in any suitable manner, including by assigned caregiver, location, alphabetical order, location within hospital 22, or in other manners. The data in this list is pulled from EMR server 52 by health info app 30. When a caregiver selects one of the patients listed in the screen 142*a* of FIG. 33, health info app 30 displays additional information about the selected patient.

Figure 34:
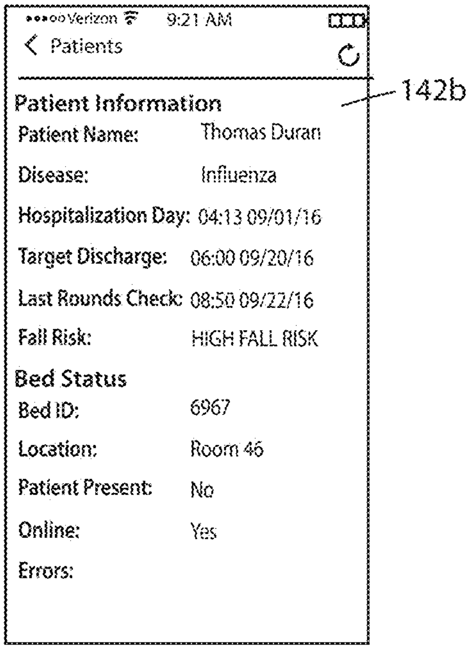
FIG. 34 is an illustrative example of a screen shot displayable on the mobile electronic device showing detailed information about a patient selected from the list of FIG. 33.
Figure 35:
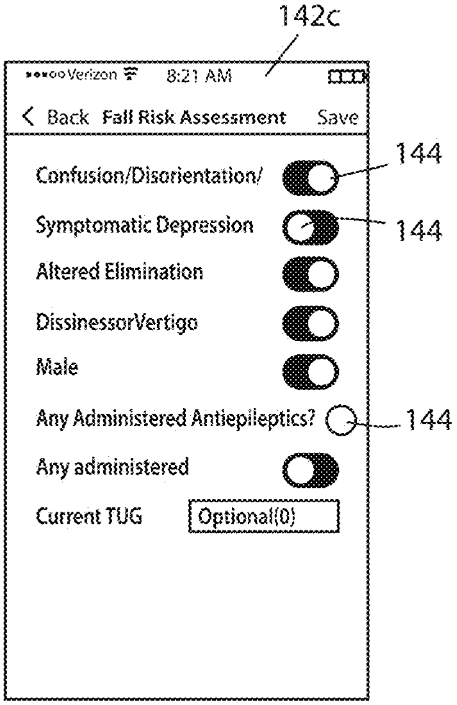
FIG. 35 is an illustrative example of a screen shot displayable on the mobile electronic device showing a fall risk assessment for a patient from the list of FIG. 33.

FIG. 34 illustrates one example of the additional information that may be displayed by health info app 30 in response to a user selecting one of the patients shown on the list of FIG. 33. Rounding screen 142*b* of FIG. 34 shows the patient's name, disease or other health condition, hospitalization date, target discharge date, last rounds check, whether the patient is a fall risk or not, and, in some embodiments, information derived from the patient's bed. The bed derived information may include the bed's ID, its location, whether the patient is present on the bed or not, whether the bed is off-line or on-line with respect to network 50, and any errors that may be present with the bed. Such information is passed from the bed to a server on network 50, such as a dedicated bed server (not shown) or other type of server, that communicates with local vendor server 48. Beds that are capable of transmitting this type of information to a hospital network are disclosed in, for example, the following commonly assigned U.S. patent applications: Ser. No. 14/692,871 filed Apr. 22, 2015, by inventors Marko Kostic et al. and entitled PERSON SUPPORT APPARATUS WITH POSITION MONITORING; Ser. No. 62/253,167 filed Nov. 10, 2015, by inventors Marko Kostic et al. and entitled PERSON SUPPORT APPARATUS WITH ACCELERATION DETECTION; and Ser. No. 14/873,734 filed Oct. 2, 2015, by inventors Marko Kostic et al. and entitled PERSON SUPPORT APPARATUSES WITH MOTION MONITORING; the complete disclosures of all of which are incorporated herein by reference.

If a caregiver selects any of the items displayed on rounding screen 142*b* of FIG. 34, health info app 30 displays additional information about that item. For example, if the user selects the fall risk item from the screen 142*b* of FIG. 34, health info app 30 displays further information regarding fall risk assessments, such as the rounding screen 142*c* of FIG. 35. Rounding screen 142*c* of FIG. 35 includes a checklist of questions for assessing the fall risk of a patient. Rounding screen 142*c* also includes slider bars 144 enabling the user to enter yes or no for each of the questions. Rounding screen 142*c* thereby assists a caregiver in determining whether or not a particular patient should be considered at risk for falling. Health info app 30 calculates a score from the answers to the listed questions and shares the score with the caregiver. The caregiver can then enter a conclusion into health info app 30 as to whether the patient is at risk of falling or not. In some embodiments, health info app 30 is configured to automatically make this determination and enter the patient's fall risk, or lack of fall risk, into the electronic medical record of the patient that is stored on EMR server 52.

Health info app 30 is supplied by vendor 24 with a set of pre-populated fall risk questions that are customizable by the administrators of hospital 22. The hospital 22 can therefore tailor their fall risk assessments in any manner that they see fit. Once tailored, health info app 30 presents the caregivers with the custom tailored questions via a screen such as that shown in FIG. 142*c* of FIG. 35. The answers to the questions are forwarded by health info app 30 to EMR server 52 for storage therein.

Figure 36:
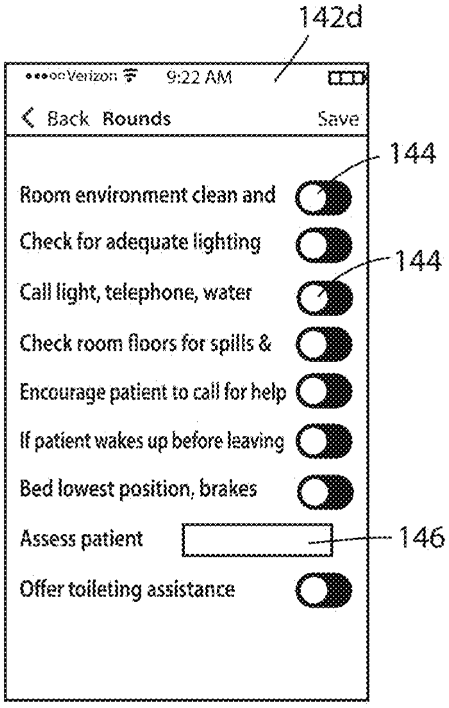
FIG. 36 is an illustrative example of a screen shot displayable on the mobile electronic device showing caregiver rounding information for a patient selected from the list of FIG. 33.

In addition to helping the caregivers assess the fall risk of patients, rounding screens 142 of health info app 30 also provide screens on which data associated with the caregivers rounding duties can be entered and automatically charted to the patient's electronic medical record, or to any other suitable server on network 50. Rounding screen 142*d* of FIG. 36 illustrates an example of such a screen. Rounding screen 142*d* includes a list of questions with slider bars 144 and/or data entry fields 146 that enable the caregiver to input answers to the questions. The questions are designed to document tasks, patient conditions, and other items associated with the rounding duties of caregivers. As with the fall risk assessment questions, health info app 30 is supplied by vendor 24 with a list of prepopulated rounding questions that are customizable by the hospital 22. The answers to the question are forwarded by the devices 32 to local vendor server 48 which, in turn, forwards the information to the appropriate server on network 50, such as, but not limited to, EMR server 52.

Figure 37:
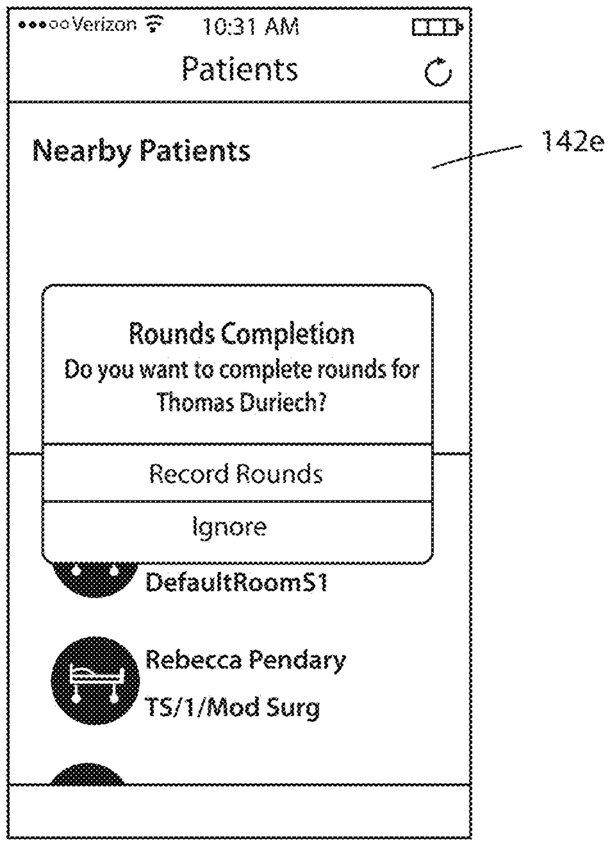
FIG. 37 is an illustrative example of a screen shot displayable on the mobile electronic device inquiring if a caregiver wishes to save rounding information previously entered.

FIG. 37 illustrates an example of a rounding screen 142*e* that may be displayed by health info app after a caregiver has completed all of the questions associated with their rounding duties. Screen 142*e* asks the caregiver is he or she would like to complete the rounds for a particular patient. If yes, health info app 30 saves the answers and forwards them to the appropriate recipients on network 50. If no, health info app 30 does not forward the results to network 50.

Figure 38:
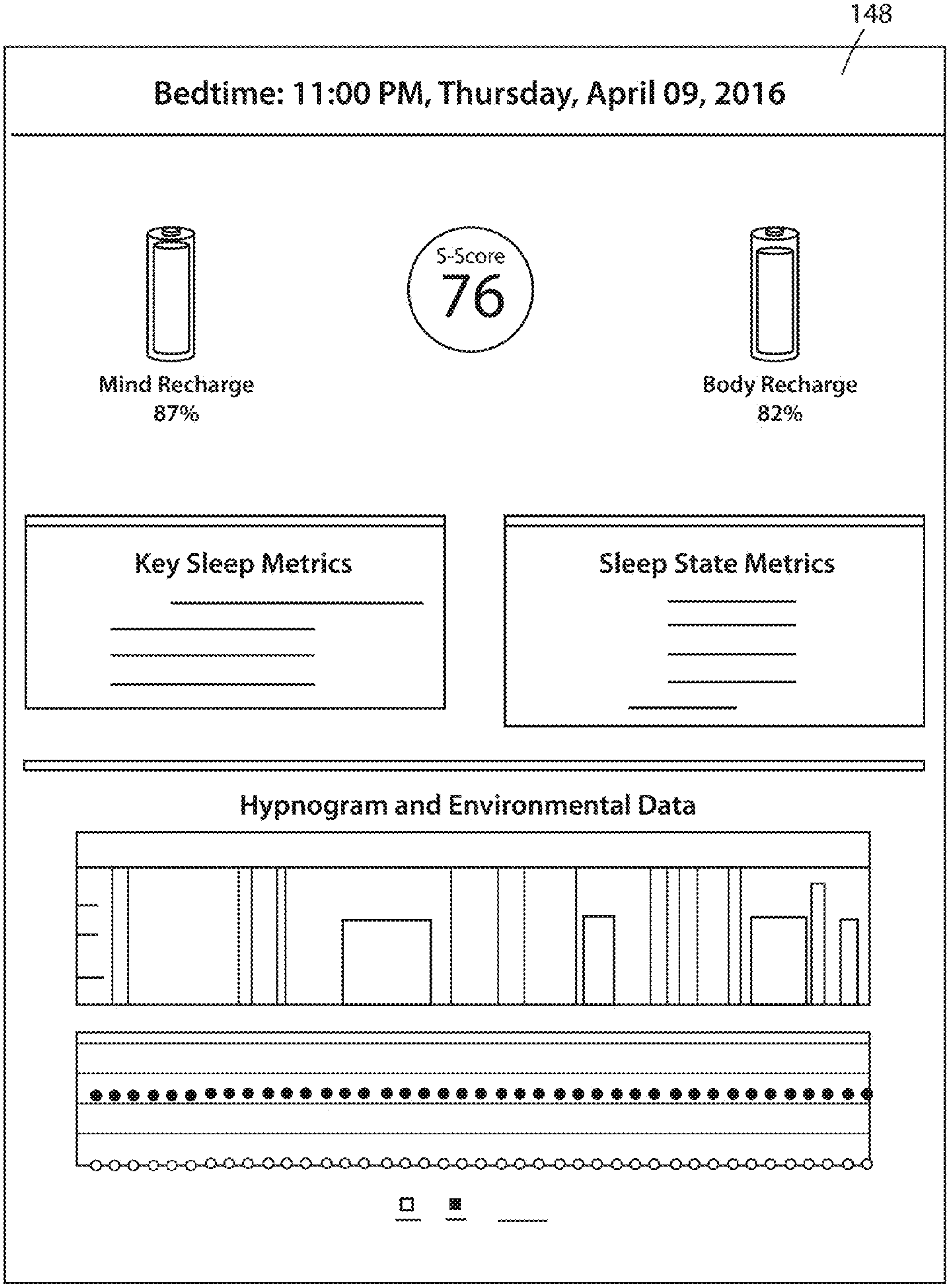
FIG. 38 is an illustrative example of a screen shot displayable on the mobile electronic device showing patient sleep information.

FIG. 38 illustrates an environmental summary screen 150 that is displayable by health info app 30 to authorized users. Environmental summary screen 150 displays data regarding the environmental conditions of a patient's room, including data regarding the sleep quality of the patient. The displayed sleep quality data (including the classification of the different types and amounts of sleep) is gathered in any of the same manners discussed above with respect to FIG. 11. The light, noise, and temperature data is gathered from light, noise, and temperature sensors positioned in the patient rooms. In some embodiments, health info app 30 is configured to use the sleep quality information, as well as the light, noise, and/or temperature information, to compute a sleep score 150. The sleep score is displayed on screen 148, as well as one or more of the other summary screens discussed herein (e.g. summary screens 122).

Figure 39:
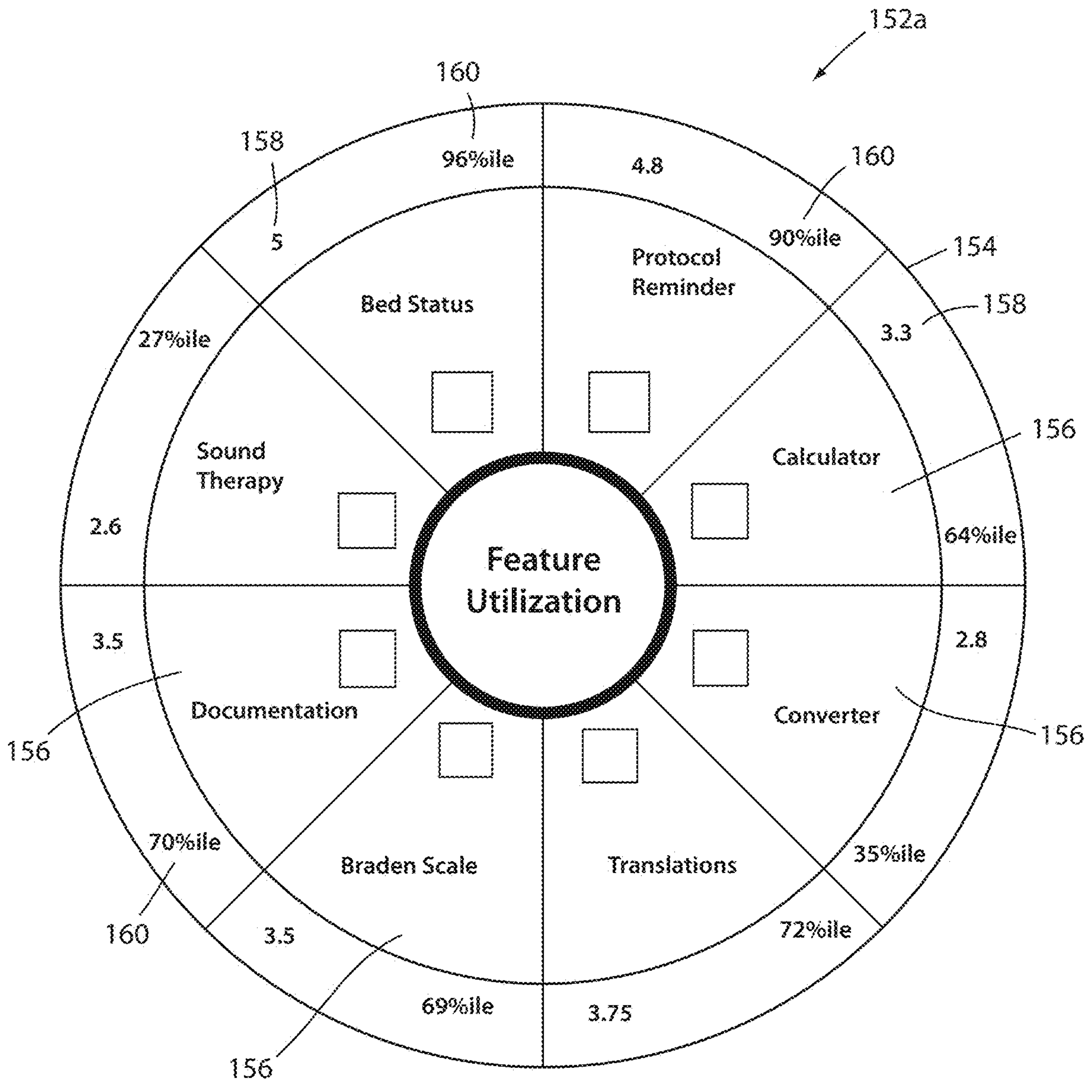
FIG. 39 is an illustrative example of a screen shot displayable on the mobile electronic device showing feature utilization of a medical device.
Figure 40:
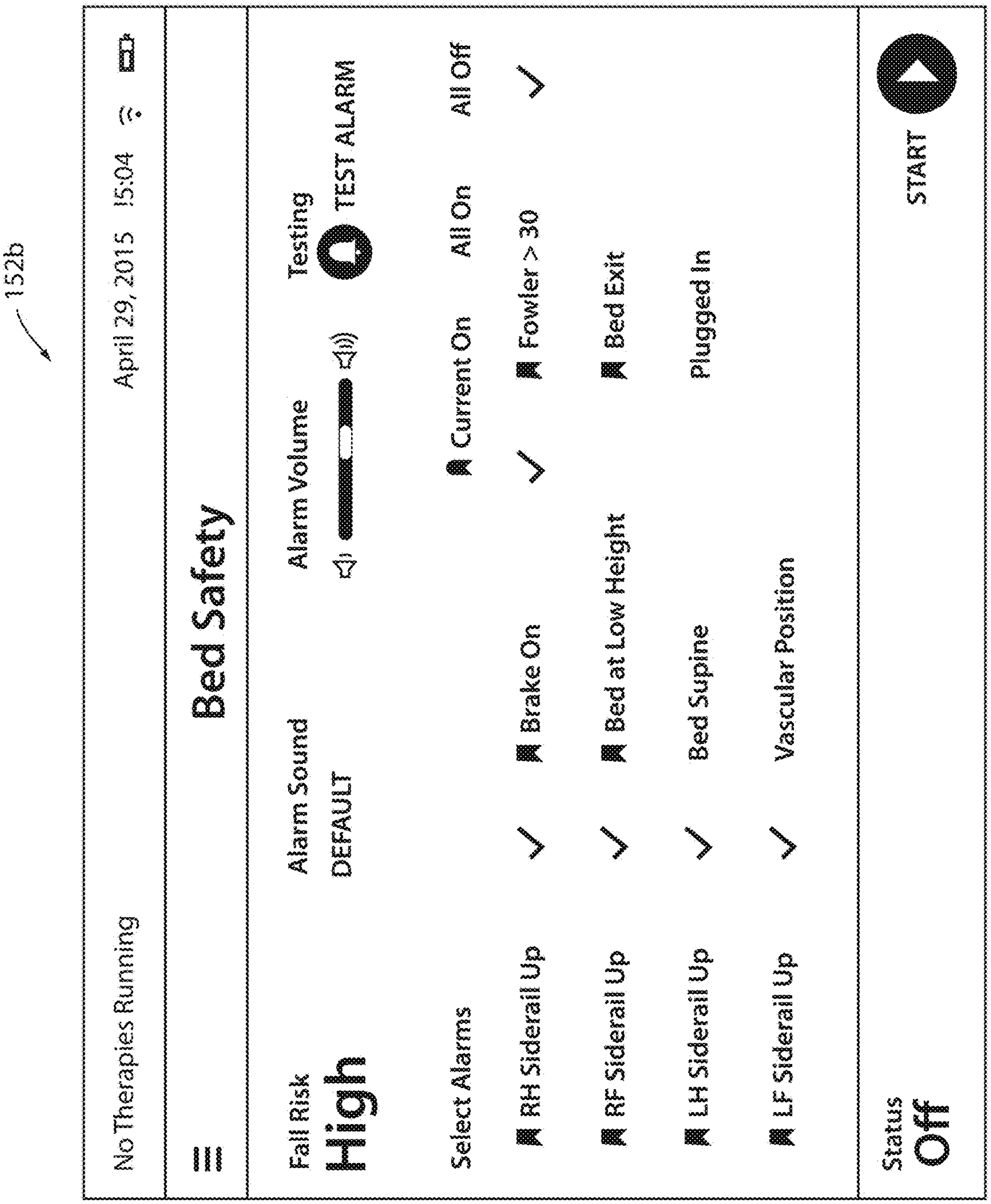
FIG. 40 is an illustrative example of a screen shot displayable on the mobile electronic device showing status information regarding a medical device.
Figure 41:
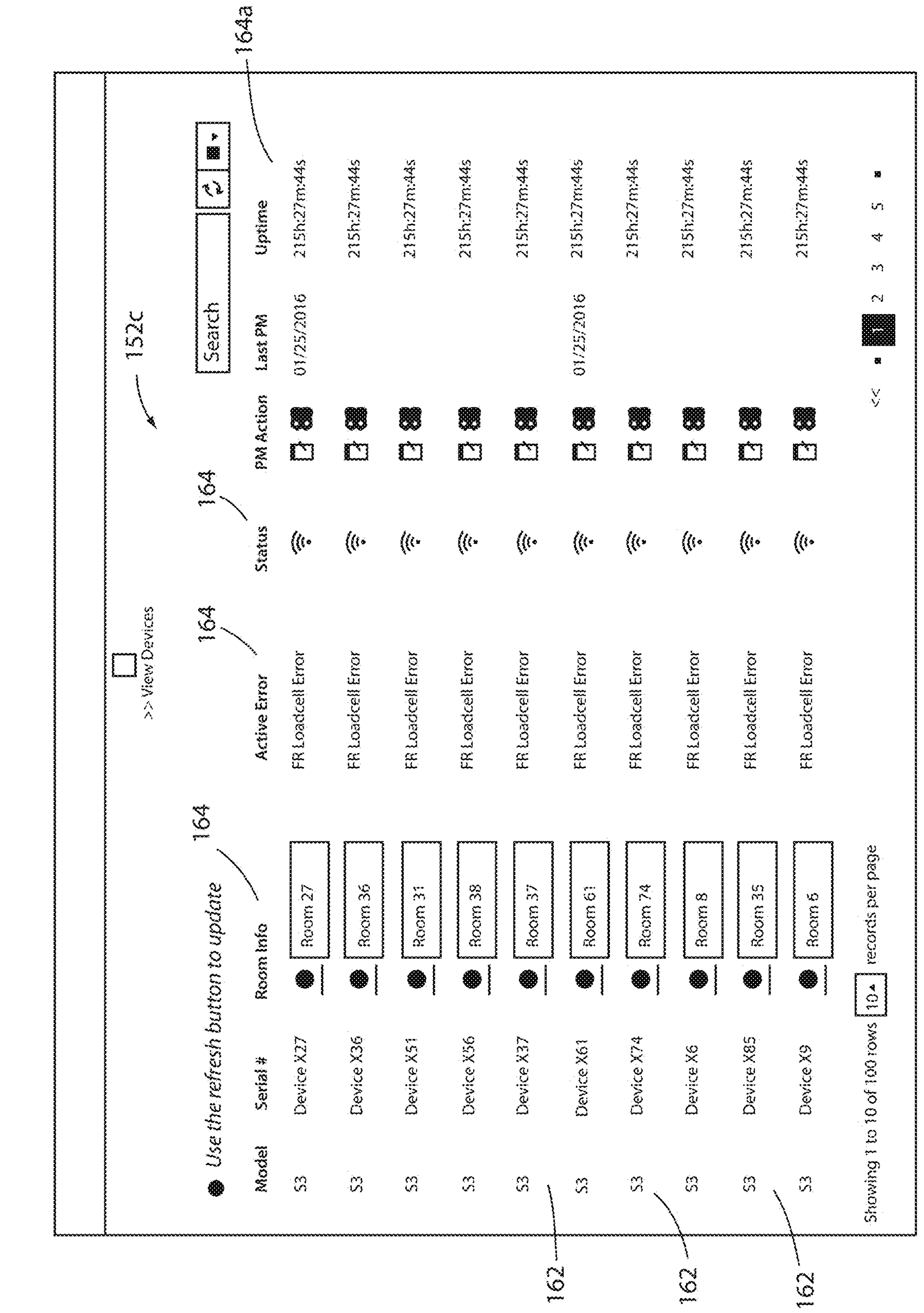
FIG. 41 is an illustrative example of a screen shot displayable on the mobile electronic device showing status information regarding a fleet of medical devices.

FIGS. 39-41 illustrate examples of medical equipment screens 152 that may be displayed by health info app 30. Medical equipment screens 152, in the examples shown in these FIGS., provide information regarding the beds of the patients 34*d*. It will be understood, however, that screens 152 are not limited to displaying information gathered from the patient's beds, but may also or alternatively include information gathered from any other medical devices used within hospital 22. When screens 152 show information from the hospital's beds, such information is transmitted by the beds to a server on network 50 that shares the bed information with local vendor server 48. Various conventional beds may be used that are capable of reporting data regarding their use and status to a hospital's local area network. Suitable examples of such beds are disclosed in the following commonly assigned U.S. patent applications: Ser. No. 14/819,844 filed Aug. 6, 2015, by inventors Krishna Bhimavarapu et al. entitled PATIENT SUPPORT APPARATUSES WITH WIRELESS HEADWALL COMMUNICATION; Ser. No. 15/075,747 filed Mar. 21, 2016, by inventors Michael Hayes et al. and entitled LOCATION DETECTION SYSTEMS AND METHODS; Ser. No. 15/185,623 filed Jun. 17, 2016, by inventors Marko Kostic et al. and entitled PATIENT SUPPORT APPARATUSES WITH LOAD CELLS; and Ser. No. 14/212,367 filed Mar. 14, 2014, by inventors Michael Hayes et al. and entitled PATIENT SUPPORT APPARATUS WITH PATIENT INFORMATION SENSORS; the complete disclosures of all of which are incorporated herein by reference.

FIG. 39 illustrates a medical equipment screen 152*a* that summarizes the feature utilization of a piece of medical equipment, such as a patient bed. Screen 152*a* is only displayed to authorized users 34, such as, but not limited to, service technicians and/or administrators. Medical equipment screen 152*a* includes a circle 154 that is divided into a plurality of sections 156. Each section 156 corresponds to a different feature or set of features of the bed. For example, circle 154 of FIG. 39 is divided into eight sections 156 that correspond to the following features of a bed: protocol reminder, calculator, converter, translations, Braden scale, documentation, sound therapy, and bed status.

Each of these sections refers to different features that are provided by particular beds. The protocol reminder is a built-in feature that reminds caregivers of times and/or steps to be taken for different protocols. The calculator feature is an electronic calculator that is accessible via a screen of the bed and usable to perform calculations. The converter feature is a mathematical function that is accessible via a screen of the bed to allow a user to convert measurements expressed in a first type of units to another type of units (e.g. pounds to kilograms). The translation feature is a feature of the bed that translates words and/or speech from one language to another. The Braden scale feature is a series of questions and/or instructions that are displayable on a screen of the bed for assisting caregivers in assigning a Braden scale score to a patient. The documentation feature is a feature that allows patient data to be documented automatically via the bed to EMR server 52. The sound therapy feature is a feature that allows a user to select music, or other desired sounds, to be played on the speakers of the bed. The bed status feature is a feature that allows the bed to transmit data regarding its usage and status to network 50. Such data may include, but is not limited to, status regarding the bed's siderails, the height of its litter frame, whether the brakes are activated or not, the state of an exit detection system, the presence or absence of the patient, and/or other data.

Each section 156 of circle 154 includes statistics regarding the usage of these different features. Specifically, as shown in FIG. 39, each section 156 includes an average number of uses of a particular bed over a certain time period, as indicated by indicators 158. Each section 156 also includes a percentile indicator 160 that indicates what percentile the frequencies of usage for those features fall into relative to the entire fleet of similar beds maintained at hospital 22. Other statistics and/or features may also or alternatively be displayed.

FIG. 40 illustrates an example of a medical equipment screen 152*b* that is displayable by health info app 30 to authorized users 34. Screen 152*b* illustrates the detailed current state of a particular medical device or piece of medical equipment. In the example shown in FIG. 152*b*, the medical device is a bed. As can be seen, medical equipment screen 152*b* illustrates detailed information about the status of the bed, such as the position of each of the bed's siderails, whether the brake is on or off, whether the bed is at its lowest height or not, whether the bed is in a vascular position, whether the Fowler section of the bed is at an angle greater than 30 degrees, whether the exit system is armed or disarmed, and whether the bed is plugged into a source of electrical power or not. Still other information may be displayed by the bed, such as, but not limited to, a volume of the alarms for that bed and/or a style of sound for the alarms for that bed. The patient's fall risk may also be indicated on screen 152*b*. The specific content of medical equipment screen 152*b* may vary from that shown, depending upon the sensors, features, and capabilities of the beds used in hospital 22. Further, the specific content of medical equipment screen 152*b* will change when used to display information regarding equipment other than beds.

FIG. 41 illustrates another example of a medical equipment screen 152*c* that is displayable by health info app 30 to authorized users. Medical equipment screen 152*c* is a screen that shows the status of a fleet of medical devices, rather than the status of an individual medical device, such as is shown on screen 152*b*. The status of the displayed medical devices is abbreviated in comparison to the detailed list of information provided via screens 152*b*. Each medical device shown on screen 152*c* is listed in its own row 162. Each column 164 illustrates a different piece of information about the device. Health info app 30 is programmed to allow the user 34 to sort the medical devices in any desired manner, such as by type, location, status, etc. Further, health info app 30 is programmed to allow a user to sort the list according to each of the characteristics identified in the heading of each column. Thus, for example, if a user wished to display the devices in the order of highest or least amount of uptime—as indicated in column 164*a*—he or she can instruct health info app 30 to do so. In some embodiments, health info app 30 is also configurable to allow the user to select what columns are to be displayed on medical equipment screens, such as screen 152, as well as the order in which the columns are arranged.

Figure 42:
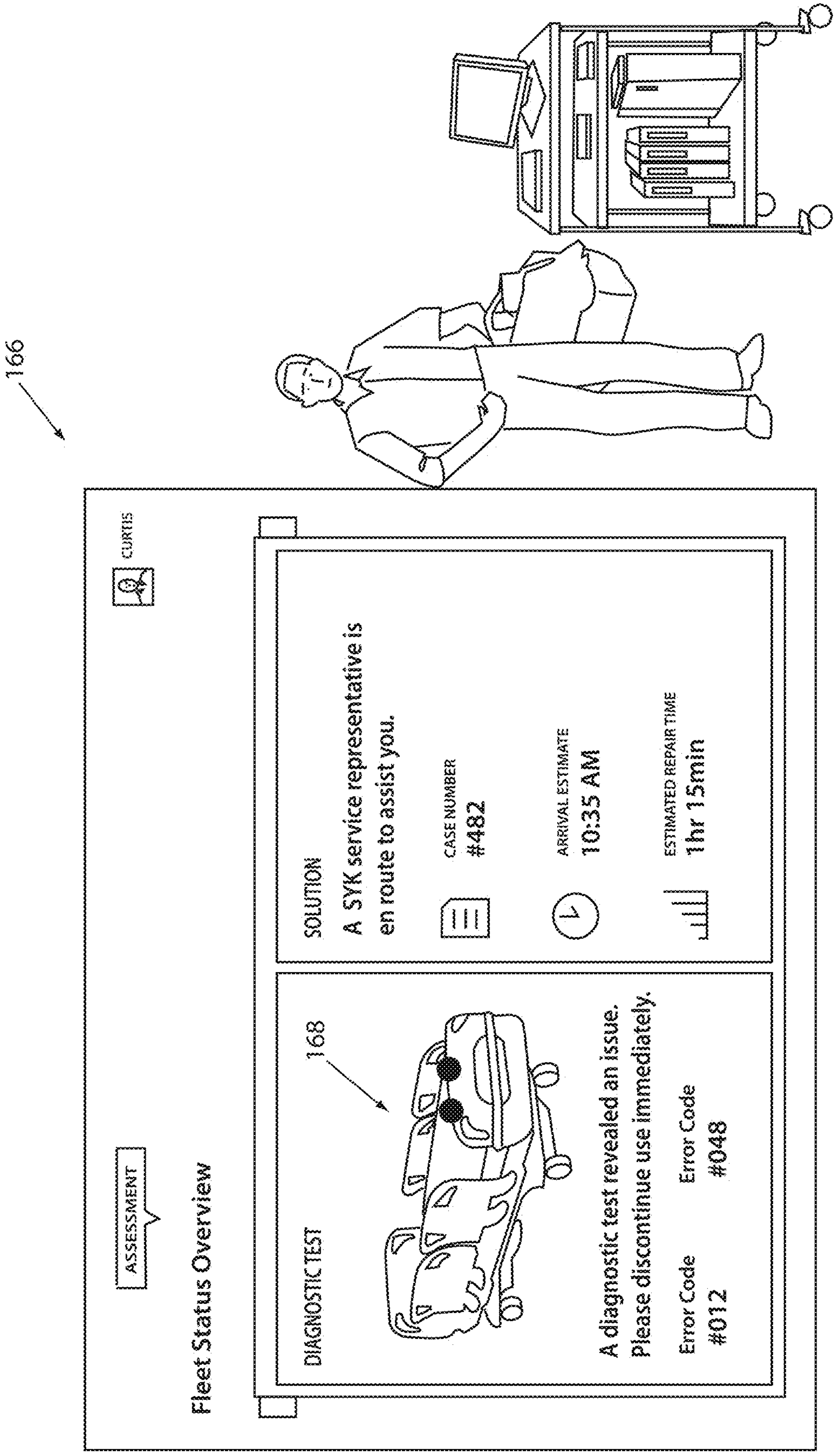
FIG. 42 is an illustrative example of a screen shot displayable on the mobile electronic device showing information regarding servicing of a medical device.

FIG. 42 illustrates an example of a service screen 166 that is displayable by health info app 30 to authorized users 34. Service screen 166 may be displayed in response to selecting a particular column of screen 152*c* relating to service status, or it may be selected in other manners. Service screen 166 provides information regarding the servicing of a specific piece of medical equipment. In the example shown in FIG. 42, the specific piece of medical equipment is a patient bed. Other types of medical equipment, however, can have their service status information imported into health info app 30. Regardless of which specific pieces of medical equipment are incorporated into health info app 30, health info app 30 retrieves the service status information for these medical devices via communication with local vendor server 48, which in turn communicates with a server on network 50 that contains service information for equipment at hospital 22. In some embodiments, local vendor server 48 may communicate via Internet connection 38 with vendor cloud 36 and/or other another vendor's computer system in which servicing information for the medical equipment is stored.

Service screen 166 identifies the piece of medical equipment and, in some cases, includes a picture 168 of the equipment. If there are any error codes associated with the medical equipment, they are listed on screen 166. Screen 166 also includes information regarding a current service call, if any, and past servicing information for that particular medical device. For example, service screen 166 shows an expected time or arrival of a service appointment, an estimate of how long the servicing will last, a case number for the service call, and any other information that may be relevant to a service call.

Service screen 166 is primarily intended for use by technicians or other personnel involved in the servicing of the equipment at hospital 22. In some embodiments, screen 166 is used by service tech vendor 34*f*, or by a service technician associated with the vendor of the piece of medical equipment shown on screen 166. Health info app 30 is also configured to not only show service information on screen 166, but to allow users of app 30 to enter service data onto these screens 166, including requesting servicing for a particular medical device. Caregivers and other users 34 of health info app 30 can therefore easily request service of a piece of equipment if they notice it is malfunctioning, or otherwise in need of service, while they are performing their everyday activities, thereby improving the speed at which servicing takes place.

It will be understood that the principles disclosed herein can be embodied as a software application in which instructions for one or more processors are tangibly and non-transitorily fixed in a computer-readable medium. The instructions, when executed by the one or more processors, carry out any one or more of the health information functions described herein.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A system comprising a plurality of patient support apparatuses, a first server, and a mobile device software application;

wherein each of the patient support apparatuses includes:

(a) a litter frame adapted to support a patient thereon;

(b) a plurality of siderails;

(c) a wheel;

(d) a brake for the wheel;

(e) an exit detection system adapted to issue an exit alert when a patient exits the corresponding patient support apparatus;

(f) a lift subsystem adapted to change a height of the litter frame;

(g) a network transceiver adapted to communicate with the first server; and (h) a controller adapted to transmit patient support apparatus data to the first server via the network transceiver, the patient support apparatus data including at least one of the following: a position of a siderail of a particular patient support apparatus of the plurality of patient support apparatuses, a status of a brake of the particular patient support apparatus, a height of a litter frame of the particular patient support apparatus, or a status of the exit detection system of the particular patient support apparatus;

wherein the first server is adapted to transmit the patient support apparatus data to a mobile electronic device on which the mobile device software application is installed; and wherein the mobile device software application is embodied as a non-transitory computer readable medium with computer executable instructions stored therein that are adapted to be executed by a processor of the mobile electronic device, the computer executable instructions, when executed, are adapted to cause the processor to perform the following:

display on the display of the mobile electronic device a plurality of patients;

in response to a caregiver selecting a particular one of the patients, perform the following:

display on the display of the mobile electronic device the patient support apparatus data corresponding to the patient support apparatus associated with the selected patient;

display on the display of the mobile electronic device rounding data relating to the caregiver's performance of his or her rounding duties for the selected patient;

receive rounding information from the caregiver regarding a performance of his or her rounding duties for the selected patient;

transmit the rounding information to a computer network of a healthcare facility; and receive service data for the patient support apparatus associated with the selected patient from a vendor server and, in response to a caregiver selecting a service screen, display on the display of the mobile electronic device the service data on the service screen, wherein the service data indicates at least one of the following: (a) an estimate of a time at which service will be performed, or (b) an estimate of the length of time the service will take to be performed.

2. The system of claim 1 wherein the computer executable instructions, when executed, are further adapted to cause the processor to display fall risk data on the display of the mobile electronic device, wherein the fall risk data indicates a fall risk of a patient assigned to the particular patient support apparatus.

3. The system of claim 1 wherein the computer executable instructions, when executed, are further adapted to cause the processor to:

receive location information from the first server, the location information identifying a location of the particular patient support apparatus within the healthcare facility; and display the location of the particular patient support apparatus within the healthcare facility on the display of the mobile electronic device.

4. The system of claim 1 wherein the computer executable instructions, when executed, are further adapted to cause the processor to:

receive patient presence information from the first server, the patient presence information identifying whether the patient is present on the particular patient support apparatus or not; and display the patient presence information on the display of the mobile electronic device.

5. The system of claim 1 wherein the computer executable instructions, when executed, are further adapted to cause the processor to display a name of a patient assigned to the particular patient support apparatus on the display of the mobile electronic device.

6. The system of claim 1 wherein the computer executable instructions, when executed, are further adapted to cause the processor to:

display on the display of the mobile electronic device a plurality of questions for assessing a fall risk of a patient assigned to the particular patient support apparatus; and receive answers to the plurality of questions from a caregiver associated with the patient.

7. The system of claim 6 wherein the computer executable instructions, when executed, are further adapted to cause the processor to calculate a fall risk score from the received answers to the plurality of questions.

8. The system of claim 6 wherein the computer executable instructions, when executed, are further adapted to cause the processor to allow an administrator of the healthcare facility to customize the plurality of questions.

9. The system of claim 1 wherein the computer executable instructions, when executed, are further adapted to cause the processor to:

retrieve patient data from an electronic medical record server in communication with the computer network of the healthcare facility; and display the patient data on the display of the mobile electronic device, wherein the patient data includes names of patients assigned to a particular caregiver.

10. The system of claim 9 wherein the patient data further includes health conditions of the patients assigned to the particular caregiver.

11. The system of claim 9 wherein the patient data further includes data indicating when rounding was last performed for the patients assigned to the particular caregiver.

12. The system of claim 1 wherein the computer executable instructions, when executed, are further adapted to cause the processor to transmit the rounding information to the first server.

13. The system of claim 1 wherein the computer executable instructions, when executed, are further adapted to cause the processor to:

retrieve patient data from an electronic medical record server in communication with the computer network of the healthcare facility;

display the patient data on the display of the mobile electronic device, wherein the patient data includes a list of patients assigned to a particular caregiver; and display additional information about a particular patient from the list of patients in response to a caregiver selecting the particular patient from the list of patients.

14. The system of claim 13 wherein the additional information includes at least one of the following: a room to which the particular patient is assigned; an indication of whether the particular patient is in patient support apparatus or out of patient support apparatus; a fall risk of the patient; or a health condition of the particular patient.

15. The system of claim 1 wherein the rounding information includes a reminder to perform at least one of the following: activate a brake of the particular patient support apparatus; put the particular patient support apparatus into a low height condition; offer toileting assistance to a patient assigned to the particular patient support apparatus; check for adequate lighting for the patient; check that a room in which the particular patient support apparatus is located is cleared of spills; or assess the patient.

16. The system of claim 1 wherein the mobile electronic device is one of a smart phone or a tablet computer.

17. The system of claim 1 wherein the patient support apparatus data further includes connectivity data indicating whether each of the plurality of patient support apparatuses is currently connected to the computer network of the healthcare facility, and wherein the computer executable instructions, when executed, are further adapted to cause the processor to display on the display of the mobile electronic device the connectivity data.

18. The system of claim 17 wherein the mobile electronic device is one of a smart phone or a tablet computer and the computer executable instructions, when executed, are further adapted to cause the processor to wirelessly retrieve the patient support apparatus data from the first server using WiFi communications between the mobile electronic device and a wireless access point of the computer network of the healthcare facility.

19. The system of claim 1 wherein the patient support apparatus data further includes electrical connection data indicating whether each of the plurality of patient support apparatuses is currently plugged into an electrical outlet, and wherein the computer executable instructions, when executed, are further adapted to cause the processor to display on the display of the mobile electronic device the electrical connection data.

20. The system of claim 19 wherein the patient support apparatus data further includes angular data indicating whether each of the plurality of patient support apparatuses has a Fowler section elevated to an angle greater than a threshold, and wherein the computer executable instructions, when executed, are further adapted to cause the processor to display on the display of the mobile electronic device the angular data.

* * * * *